United States Patent
Karp et al.

(10) Patent No.: US 9,884,129 B2
(45) Date of Patent: Feb. 6, 2018

(54) RELEASE OF AGENTS FROM CELLS

(71) Applicant: The Brigham and Women s Hospital, Inc., Boston, MA (US)

(72) Inventors: Jeffrey M. Karp, Brookline, MA (US); Debanjan Sarkar, Williamsville, NY (US); Praveen Kumar Vemula, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 436 days.

(21) Appl. No.: 14/589,037

(22) Filed: Jan. 5, 2015

(65) Prior Publication Data

US 2015/0125540 A1    May 7, 2015

Related U.S. Application Data

(62) Division of application No. 13/501,475, filed as application No. PCT/US2010/052866 on Oct. 15, 2010, now Pat. No. 8,956,863.

(60) Provisional application No. 61/251,801, filed on Oct. 15, 2009, provisional application No. 61/387,242, filed on Sep. 28, 2010.

(51) Int. Cl.

| A01N 63/00 | (2006.01) |
|---|---|
| A61K 47/48 | (2006.01) |
| A61K 38/18 | (2006.01) |
| A61K 31/573 | (2006.01) |
| A61K 31/704 | (2006.01) |
| A61K 35/28 | (2015.01) |
| C12N 5/0775 | (2010.01) |
| A61K 47/69 | (2017.01) |

(52) U.S. Cl.
CPC ...... *A61K 47/48915* (2013.01); *A61K 31/573* (2013.01); *A61K 31/704* (2013.01); *A61K 35/28* (2013.01); *A61K 38/1816* (2013.01); *A61K 47/6921* (2017.08); *A61K 47/6935* (2017.08); *A61K 47/6937* (2017.08); *C12N 5/0662* (2013.01)

(58) Field of Classification Search
None
See application file for complete search history.

(56) References Cited

U.S. PATENT DOCUMENTS

| 6,083,875 | A | 7/2000 | Sato et al. |
|---|---|---|---|
| 6,171,610 | B1 | 1/2001 | Vacanti et al. |
| 2005/0100877 | A1 | 5/2005 | Xu et al. |
| 2005/0276861 | A1 | 12/2005 | Kipp et al. |
| 2006/0280430 | A1 | 12/2006 | Rabinow et al. |
| 2007/0219526 | A1 | 9/2007 | Freyman |
| 2007/0243137 | A1 | 10/2007 | Hainfeld |
| 2008/0057027 | A1 | 3/2008 | Stolen et al. |
| 2009/0105172 | A1 | 4/2009 | Diener et al. |
| 2009/0130756 | A1 | 5/2009 | Klann et al. |
| 2012/0251443 | A1 | 10/2012 | Ozaki et al. |

FOREIGN PATENT DOCUMENTS

| WO | 2005/059118 | 6/2005 |
|---|---|---|
| WO | 2009/032994 | 3/2009 |
| WO | 2009/134866 | 11/2009 |

OTHER PUBLICATIONS

International Search Report and Written Opinion of the International Searching Authority dated Jun. 23, 2011 from International Patent Application No. PCT/US2010/052866, 14 pgs.
Aboody et al., "Neural stem cells display extensive tropism for pathology in adult brain: Evidence from intracranial gliomas," *Proc. Natl. Acad. Sci. U.S.A.* 97:12846-12851, 2000 (with correction).
Alfaro et al., "The Wnt modulator sFRP2 enhances mesenchymal stem cell engraftment, granulation tissue formation and myocardial repair," *Proc. Natl. Acad. Sci. U.S.A.* 105:18366-18371, 2008.
Brown et al., "Intravascular Delivery of Neural Stem Cell Lines to Target Intracranial and Extracranial Tumors of Neural and Non-Neural Origin," *Hum. Gene Ther.* 14:1777-1785, 2003.
Chithrani et al., "Elucidating the Mechanism of Cellular Uptake and Removal of Protein-Coated Gold Nanoparticles of Different Sizes and Shapes," *Nano Lett.* 27:1542-1550, 2007.
Chithrani et al., "Determining the Size and Shape Dependence of Gold Nanoparticle Uptake into Mammalian Cells," *Nano Lett.* 6:662-668, 2006.
Colter et al., "Rapid expansion of recycling stem cells in cultures of plastic-adherent cells from human bone marrow," *Proc. Natl. Acad. Sci. U.S.A.* 97:3213-3218, 2000.
Cotton et al., "Receptor-Mediated Transport of DNA into Eukaryotic Cells," *Methods Enzym.* 217:618, 1993.
Farokhzad et al., *Expert. Opin. Drug Deliv.* 3:311-324, 2006.
Gao et al., "Mechanics of receptor-mediated endocytosis," *Proc. Natl. Acad. Sci. U.S.A.* 102:9469-9474, 2005.
Garnett, "Targeted drug conjugates: principles and progress," *Adv. Drug. Deliv. Rev.* 53:171-216, 2001.
Garrod et al., "Targeted Lymphoid Homing of Dendritic Cells is Required for Prolongation of Allograft Survival," *J. Immunol.* 177:863-868, 2006.
Gomez-Navarro et al., "Genetically modified CD34+ cells as cellular vehicles for gene delivery into areas of angiogenesis in a rhesus model," *Gene Ther.* 7:43-52, 2000.
Gref et al., "The controlled intravenous delivery of drugs using PEG-coated sterically stabilized nanospheres," *Adv. Drug Delivery Rev.* 16:215-233, 1995.
Gref et al., "'Stealth' corona-core nanparticles surface modified by polyethylene glycol (PEG): influences of the corona (PEG chain length and surface density) and of the core composition on phagocytic uptake and plasma protein adsorption," *Colloids Surfaces B: Biointerfaces* 18:301-313, 2000.
Gref et al., "Biodegradable Long-Circulating Polymeric Nanospheres," *Science* 263:1600, 1994.
Grigoriadis et al., "Differentiation of Muscle, Fat, Cartilage, and Bone from Progenitor Cells Present in a Bone-derived Clonal Cell Population: Effect of Dexamethasone," *J. Cell. Biol.* 106:2139-2151, 1988.

(Continued)

*Primary Examiner* — Michail Belyavskyi
(74) *Attorney, Agent, or Firm* — Fish & Richardson P.C.

(57) ABSTRACT

A composition includes an isolated cell; at least one particle within said cell; and at least one active agent associated with the particle, wherein the active agent is capable of being released from the cell. A method includes administration of such a cell to a subject.

20 Claims, 14 Drawing Sheets

(56) References Cited

OTHER PUBLICATIONS

Herrlinger et al., "Neural Precursor Cells for Delivery of Replication-Conditional HSV-1 Vectors to Intracerebral Gliomas," *Mol. Ther.* 1:347-357, 2000.
International Preliminary Report on Patentability for PCT/US2010/052866, dated Apr. 26, 2012.
Javier et al., "Aptamer-Targeted Gold Nanoparticles as Molecular-Specific Contrast Agents for Reflectance Imaging," *Bioconjug. Chem.* 19:1309-1312, 2008.
Jin et al., "Size-Dependent Cellular Uptake and Explulsion of Single-Walled Carbon Nanotubes: Single Particle Tracking and a Generic Uptake Model for Nanoparticles," *ACS Nano* 3:149-158, 2009.
Karp et al., "Mesenchymal Stem Cell Homing: The Devil Is in the Details," *Cell Stem Cell* 4:206-216, 2009.
Khaldoyanidi et al., "CD44 variant-specific antibodies trigger hemopoiesis by selective release of cytokines from bone marrow macrophages," *Blood* 99:3955-3961, 2002.
Klibanov et al., "Amphipathic polyethyleneglycols effectively prolong the circulation time of liposomes," *FEBS Lett.* 268:235, 1990.
Koc et al., "Bone marrow-derived mesenchymal stem cells remain host-derived despite successful hematopoietic engraftment after allogeneic transplantation in patients with lysosomal and peroxisomal storage diseases," *Exp. Hematol.* 27:1675-1681, 1999.
Latil et al., "VEGF Overexpression in Clinically Localized Prostate Tumors and Neuropilin-1 Overexpression in Metastatic Forms," *Int. J. Cancer* 89:167-171, 2000.
Lien et al., "Restoration of Bone Mass and Strength in Glucocorticoid-Treated Mice by Systemic Transplantation of CXCR4 and Cbfa-1 Co-Expressing Mesenchymal Stem Cells," *J. Bone Miner. Res.* 24:837-848, 2009.
Menon et al., "Mesenchymal stromal cells as a drug delivery system," Stembook, Ed., The Stem Cell Research Community, StemBook, doi/10.3824/stembook.1.35.1, http://www.stembook.org/ (Jan. 15, 2009).
Morizono et al., "Multilineage Cells from Adipose Tissue as Gene Delivery Vehicles," *Human Gene Ther.* 14:59-66, 2003.
North et al., "Prostaglandin E2 regulates vertebrate haematopoietic stem cell homeostasis," *Nature* 447:1007-1011, 2007.
Panyam et al., "Dynamics of Endocytosis and Exocytosis of Poly(D,L-Lactide-co-Glycolide) Nanoparticles in Vascular Smooth Muscle Cells," *Pharm Res.* 20:212-220, 2003.
Pasqualini et al., "Searching for a Molecular Address in the Brain," *Mol. Psychiatry* 1:421-422, 1996.
Peer et al., "Nanocarriers as an emerging platform for cancer therapy," *Nat. Nanotech.* 2:751-760, 2007.
Pereboeva et al., "Approaches to Utilize Mesenchymal Progenitor Cells as Cellular Vehicles," *Stem Cells* 21:389-404, 2003.
Rajotte et al., "Molecular Heterogeneity of the Vascular Endothelium Revealed by In Vivo Phage Display," *J. Clin. Invest.* 102:430-437, 1998.
Sahoo et al., "Enhanced Antiproliferative Activity of Transferrin-Conjugated Paclitaxel-Loaded Nanoparticles is Mediated via Sustained Intracellular Drug Retention," *Mol. Pharm.* 2:373-383, 2005.
Sarkar et al., "Chemical Engineering of Mesenchymal Stem Cells to Induce a Cell Rolling Response," *Bioconjug. Chem.* 19:2105-2109, 2008.
Sasportas et al., "Assessment of therapeutic efficacy and fate of engineered human mesenchymal stem cells for cancer therapy," *Proc. Natl. Acad. Sci. U.S.A.* 106:4822-4827, 2009.
Studeny et al., "Mesenchymal Stem Cells: Potential Precursors for Tumor Stroma and Targeted-Delivery Vehicles for Anticancer Agents," *J. Natl. Cancer Inst.* 95:1593-1603, 2004.
Takizawa et al., "Enhanced engraftment of hematopoietic stem/progenitor cells by the transient inhibition of an adaptor protein, Lnk," *Blood* 107:2968-2975, 2006.
Thompson et al., "Mechanism of Action of Glucocorticoids," *Metabolism* 23:159-202, 1974.
Torchilin, "Drug targeting," *Eur. J. Pharm. Sci.* 11:S81-S91, 2000.
Vertut-Doi et al., "Binding and uptake of liposomes containing a poly(ethylene glycol) derivative of cholesterol (stealth liposomes) by the macrophage cell line J774: influence of PEG content and its molecular weight," *Biochim. Biophys. Acta Biomembranes* 1278:19-28, 1996.
Win et al., "Effects of particle size and surface coating on cellular uptake of polymeric nanoparticles for oral delivery of anticancer drugs," *Biomaterials* 26:2713-2722, 2005.
Xu et al., "Tracking Mesenchymal Stem Cells with Iron Oxide Nanoparticle Loaded Poly(lacticde-co-glycolide) Microparticles," *Nano Lett.* 12:4131-4139, 2012.
Yokoyama et al., "Toxicity and Antitumor Activity against Solid Tumors of Micelle-forming Polymeric Anticancer Drug and Its Extremely Long Circulation in Blood," *Cancer Res.* 51:3229, 1991.
Zhao and Karp, "Controlling Cell Fate In Vivo," *Chembiochem* 10:2308-2310, 2009.
European Office Action in European Application No. 10824174.6, dated Mar. 9, 2017, 4 pages.
Supplementary European Search Report issued in EP10824174 dated Apr. 24, 2015 (7 pages).

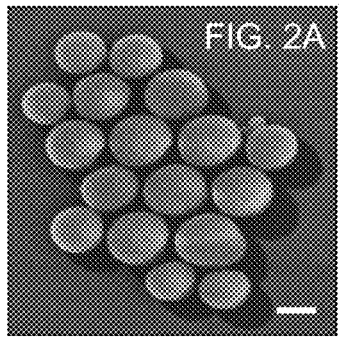
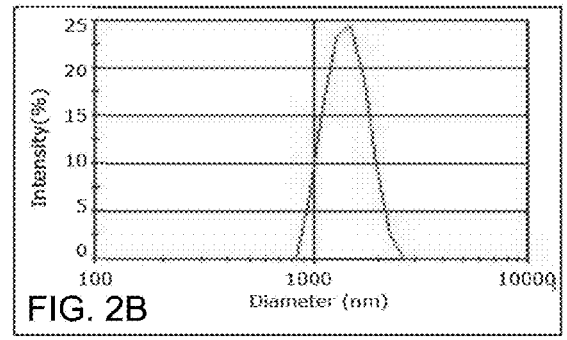
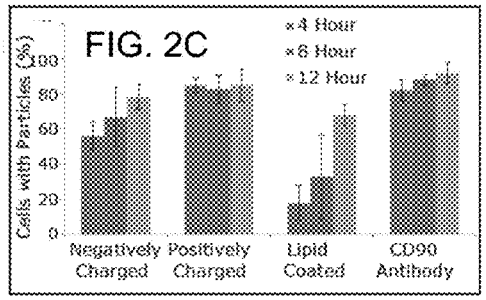
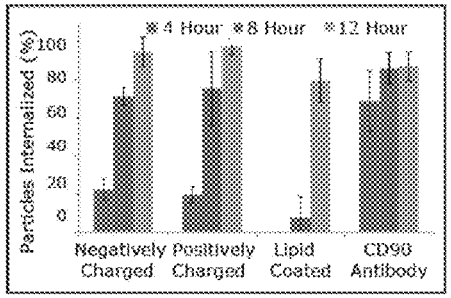
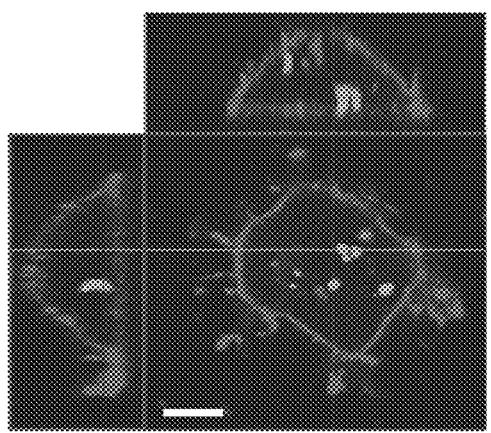
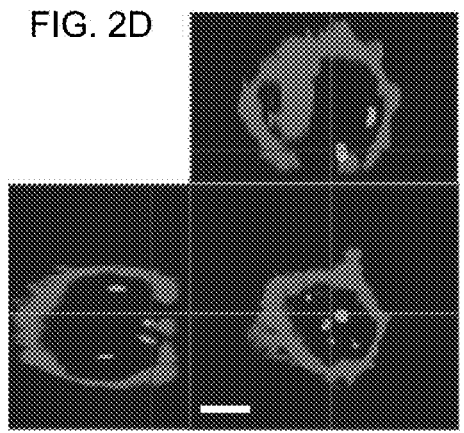
FIG. 2E   FIG. 2F

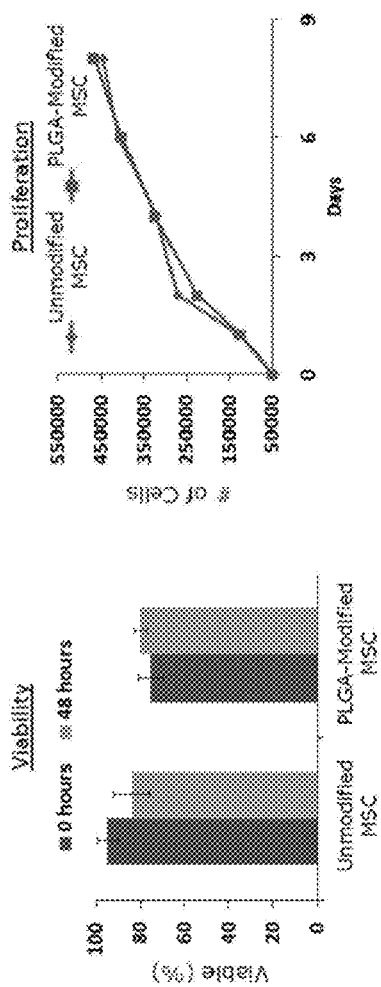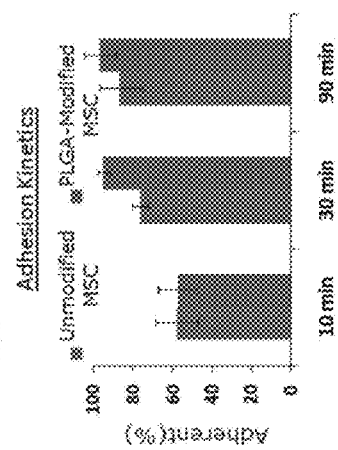
FIG. 8A
FIG. 8B
FIG. 8C

US 9,884,129 B2

RELEASE OF AGENTS FROM CELLS

CROSS REFERENCE TO RELATED APPLICATIONS

This application is a divisional of U.S. patent application Ser. No. 13/501,475, filed on Apr. 12, 2012, which is a U.S. National Phase Application under 35 U.S.C. §371 of International Application No. PCT/US2010/052866, filed on Oct. 15, 2010, which claims priority to U.S. Provisional Patent Application Nos. 61/251,801, filed on Oct. 15, 2009, and 61/387,242, filed on Sep. 28, 2010, each of which is incorporated herein by reference in its entirety.

STATEMENT AS TO FEDERALLY SPONSORED RESEARCH

This invention was made with Government support under Grant Nos. HL097172, HL095722, and DE019191, awarded by the National Institutes of Health. The Government has certain rights in the invention.

TECHNICAL FIELD

This invention relates to methods of drug delivery and controlling cell fate using cells containing internalized particles.

BACKGROUND

Control of cell fate and the extracellular environment are critical for tissue regeneration and cell therapy. During development, for example, cells are instructed by a complex set of microenvironmental cues, comprising soluble mediators and direct contacts with extracellular matrix and neighboring cells that are precisely regulated in time and space (Murry et al., 2008, Cell, 132:661-680). Consequently, when the microenvironmental balance is altered, cells can be activated toward homeostatic responses, such as to the regeneration of damaged tissues, or to pathologic changes in cell phenotype resulting in aberrant cell growth or loss of function.

Current methods to control cell fate in culture include: i) genetic manipulation of cells to program a desired phenotype, ii) addition of drugs or growth factors to the culture media, and iii) presentation of an engineered extracellular environment. Genetic modification has been used to program cell fate in culture to promote expression of specific cell surface receptors and to drive production of therapeutic peptides and proteins (Kumar et al., 2007, FASEB J., 21:3917-27; Haider et al., 2008, Circ. Res., 103:1300-08; Gnecchi et al., 2005, Nat. Med., 11:367-368; Gnecchi et al., 2006, FASEB J., 20:661-669; Sasportas et al., 2009, Proc. Natl. Acad. Sci. USA, 106:4822-27; Mangi et al., 2003, Nat. Med., 9:1195-1201). However, these modifications can exhibit a long-term impact on the cells, can be limited to agents that can be manufactured by cells, and aside from use of genetic switches, there may be an inability to finely tune the release kinetics of these agents.

Drugs or growth factors can be added to culture media to mimic a tissue microenvironment, however all cells typically receive essentially the same signal, and application of soluble factors for controlling the fate of transplanted cells is typically limited to pre-conditioning regimens. Alternatively, scaffolds or 2D/3D micro/nano-engineered substrates are useful to create multiple distinct microenvironments within a single culture system. These types of substrates have been used extensively to study cell-cell interactions, transplant cells, or mimic stem cell niches in vitro through support of cell proliferation, differentiation, or migration via controlled presentation of soluble cues and adhesive interactions (Lutolf et al., 2009, Nature, 462:433-4411; Discher et al., 2009, Science, 324:1673-77; Albrecht et al., 2006, Nat. Methods, 3:369-375; Mooney et al., 2008, Cell Stem Cell, 2:205-213). In addition, cues such as growth factors can be chemically immobilized to the substrate, providing specific locations to modulate cell behavior (Fan et al., 2007, Stem Cells, 25:1241-51; Davis et al., 2005, Circ. Res., 97:8-15; Luo et al., 2004, Nat. Mater., 3:249-253). However, these strategies typically require cells to be on, or in close proximity to the substrate. Engineering substrates to control cell phenotype and function often involves a complex manufacturing methodology and there are several circumstances under which it may be desirable to infuse cells in vivo without the use of a carrier or substrate (e.g., systemic cell infusion) (Karp et al., 2009, Cell Stem Cell, 4:206-216).

Thus, there is a need to exert control over cells and their microenvironment without genetic modification or the use of an engineered substrate.

SUMMARY

Disclosed herein are methods and compositions that can be used for controlling the cellular microenvironment through simple biomaterial-based cell modification approaches independent of genetic manipulation or the presence of an artificial substrate. In some embodiments, the disclosed methods and compositions use readily internalized biodegradable particles containing phenotype altering agents that can be used to control cell fate. The invention is based, at least in part, on the discovery that biodegradable particles that include active agents can be internalized within cells, leading to release of the agents from the particles and export of the agents from the cells. In some embodiments, the cells with internalized particles can be cryopreserved and maintain functionality.

In one aspect, the disclosure features a composition that includes an isolated cell; at least one particle within the cell; and at least one active agent associated with the particle, wherein the active agent is capable of being released from inside the cell independently of the particle. In some embodiments the active agent is capable of being release from inside the cell independently of the particle (e.g., while the cell remains intact).

In another aspect, the disclosure features a cryopreserved composition that includes an isolated cell (e.g., a viable cell) and a particle associated with an active agent, wherein the composition is at a temperature below 0° C. (e.g., below −10° C., below −20° C., below −30° C., below −40° C., below −50° C., below −60° C., below −70° C., below −80° C., below −90° C., below −100° C., below −120° C., or below −140° C.). In some embodiments, the particle is within the cell. In some embodiments, the active agent is capable of being released from the particle and/or cell (e.g., wherein the cell is intact) following thawing of the composition.

In another aspect, the disclosure features methods of delivering an active agent to a target, e.g., a region within a subject (e.g., a tissue, pathological site, tumor, or cell). The methods can include providing an isolated cell comprising a particle within the cell, wherein the particle is associated with an active agent; and contacting the target with the isolated cell, wherein the active agent is released from the cell independently of the particle (e.g., while the cell remains intact), thereby delivering the active agent to the target. In some embodiments, the target is a site within a subject distant from a location of injection or implantation of the cell.

In another aspect, the disclosure features methods of controlling the release of an active agent. The methods can include contacting a particle that includes an active agent with a cell and allowing the cell to internalize the particle, wherein the active agent then dissociates from the particle and is released from the cell (e.g., while the cell remains intact), thereby controlling the release of the active agent.

In another aspect, the disclosure features methods of controlling an activity of a cell (e.g., hematopoiesis, engraftment, motility, homing, differentiation, proliferation, survival, gene expression, and/or extracellular secretion). The methods can include providing a first isolated cell that includes a particle associated with an active agent (e.g., an agent that can control an activity of a second cell), wherein the active agent dissociates from the particle and is released from the first cell (e.g., while the cell remains intact), and contacting a second cell with the active agent, such that the active agent controls the activity of the second cell. In some embodiments, the first and second cells are the same cell. In some embodiments, one or both of the first and second cells are a stem cell or progenitor cell. In some embodiments, the second cell is a cell within a subject (e.g., a cell of the subject).

In another aspect, the disclosure features methods that include obtaining a cell from a subject; contacting the cell or a progeny thereof with a particle associated with an active agent; and administering the cell and particle to the subject. In some embodiments, the cell or a progeny thereof is incubated with the particle for a period of time (e.g., about 30 minutes, about 1 hour, about 2 hours, about 3 hours, about 4 hours, about 5 hours, about 6 hours, about 7 hours, about 8 hours, about 9 hours, about 10 hours, about 12 hours, about 15 hours, about 17 hours, about 20 hours, about 24 hours or more) prior to administering the cell and particle to the subject. In some embodiments, the methods further include ascertaining whether the particle is attached and/or internalized within the cell prior to administering the cell and particle to the subject.

In some embodiments of the above compositions and methods, the particle is biodegradable.

In some embodiments of the above compositions and methods, the particle is formulated to release the agent into the cell in a controlled or predictable manner. In some embodiments of the above compositions and methods, the particle is formulated to release the agent to the extracellular environment. In some embodiments of the above compositions and methods, the particle is formulated for delayed release of the agent (e.g., in a solution or in a cell) over a period of at least 1, 3, 5, 7, or 10 days. In some embodiments of the above compositions and methods, release of the agent from the cell and/or particle does not require an external stimulus and/or does not require cell death. In some embodiments of the above compositions and methods, release of the agent from the cell is altered (e.g., enhanced) upon cell stress or death. In some embodiments of the above compositions and methods, the agent is released by degradation, dissolution, erosion, and/or swelling of the particle, desorption and/or dissociation of the agent from the particle, diffusion of the agent away from the particle, and/or through absorption of energy (e.g., light, ultrasound, heat, IR, or UV).

In some embodiments of the above compositions and methods, the particle is between 1 nm and 100 µm in size (e.g., between 1 nm and 1000 nm in size, between 1 nm and 10 µm in size, between 1 nm and 100 nm in size, between 10 nm and 100 µm in size, between 10 nm and 10 µm in size, between 10 nm and 1000 nm in size, between 10 nm and 100 nm in size, between 10 nm and 100 µm in size, between 10 nm and 10 µm in size, between 100 nm and 1000 nm in size, between 1 µm and 10 µm in size, between 1 µm and 100 µm in size, between 500 nm and 5 µm in size, or between 500 nm and 2 µm in size, between 1 µm and 2 µm in size, between 1 µm and 8 µm in size). In some embodiments of the above compositions and methods, the particle is at least 1 µm, 2 µm, 3 µm, 4 µm, 5 µm, 6 µm, or 7 µm in size.

In some embodiments of the above compositions and methods, the particle includes a polymer (e.g., a biodegradable or nonbiodegradable polymer). In some embodiments of the above compositions and methods, the particle includes an inorganic material.

In some embodiments of the above compositions and methods, the particle includes a targeting ligand.

In some embodiments of the above compositions and methods, the agent is a therapeutic agent (e.g., a drug, protein, enzyme, gene, nucleic acid, RNAi, or biomolecule). In some embodiments of the above compositions and methods, the agent is a diagnostic or imaging agent. In some embodiments of the above compositions and methods, the agent enhances cellular engraftment. In some embodiments of the above compositions and methods, the agent promotes cellular mobilization and/or cell homing. In some embodiments of the above compositions and methods, the agent is an immunomodulator, a chemotherapeutic agent, a chemoattractant, an angiogenesis inhibitor. In some embodiments of the above compositions and methods, the agent modulates cellular secretion. In some embodiments of the above compositions and methods, the agent is cytotoxic. In some embodiments of the above compositions and methods, the agent is not a transfection agent.

In some embodiments of the above compositions and methods, the agent is covalently attached to the particle (e.g., covalently attached to the surface of the particle or to a portion of a polymeric chain within a particle). In some embodiments of the above compositions and methods, the agent is noncovalently entrapped or encapsulated within the particle.

In some embodiments of the above compositions and methods, the cell is associated with a biomaterial.

In some embodiments of the above compositions and methods, the cell is a mammalian cell. In some embodiments of the above compositions and methods, the cell is an animal cell, bacterial cell, plant cell, or yeast cell.

In some embodiments of the above compositions and methods, the cell is a stem cell or a progenitor cell. For example, the cell can be a mesenchymal stem cell. In some embodiments of the above compositions and methods, the cell is a reprogrammed cell (e.g., a reprogrammed stem cell). In some embodiments of the above compositions and methods, the cell is a differentiated cell.

In some embodiments of the above compositions and methods, the cell exogenously expresses a second therapeutic agent.

In some embodiments of the above compositions and methods, the cell is viable (e.g., at the time the agent is released from the cell).

In some embodiments of the above compositions and methods, the cell is associated with an encapsulating material, e.g., a hydrogel.

In some embodiments of the above compositions and methods, the cell is within a composition comprising at least one extracellular particle not on or within said cell. In some embodiments, the composition comprises an encapsulating material, e.g., a hydrogel.

In some embodiments of the above compositions and methods, a composition comprising the cell is injected or implanted into a subject.

In some embodiments, the above compositions and methods are used to treat a disorder, e.g., osteoporosis, cancer, inflammatory disease, Parkinson's disease, diabetes, vascular disease, heart disease, kidney disease, liver disease, infection, sepsis, anemia, thyroid disease, blood disorders, ischemic tissues, gastrointestinal disease, skin disease, lung disease, or is used for a prophylaxis or is used as a vaccine or to promote tolerance. In some embodiments, the above compositions and methods are used in the imaging or diagnosis of a subject, structure, or disorder.

In some embodiments of the above methods and compositions, a cell containing a particle extravasates through an endothelial layer in a subject (e.g., an endothelial layer in bone marrow, muscle, cartilage, tumors, heart, lung, pancreas, liver, or prostate).

In some embodiments of the above methods, the methods further include cryopreserving and/or thawing a cell (e.g., a cell with an internalized particle).

Some embodiments of the disclosed methods and compositions can have particular advantages. The modified cells can accommodate large quantities of one or more different types of agents, because the cells can be loaded with many agent-containing particles. The amount of each agent in each particle can be controlled, controlling the uptake and release of the agents. Additionally, multiple agents can be incorporated in a single cell by including multiple agents in each particle or multiple particles containing different drugs. The release of the drug can be tailored, for example, in response to time, pH, or specific enzymes or a biological stimulus and thus accommodate a wide range of predictable and random fluctuations in disease state. In some embodiments, agents are released from cells controllably (e.g., at an approximately constant rate), as compared to a burst release which is typically observed with agents released from particles in suspension (see FIG. 3B).

Some embodiments of the disclosed methods and compositions can have the potential for an extremely low toxicity profile, as particles are loaded into cells that have natural or engineered homing potential to specific tissues. Active transport through cell migration can facilitate distribution of drugs through tissue or to a particular site or sites within a subject. In embodiments where the compositions delay release of the agents, a cell can function (e.g., migrate) within a subject prior to the release of at least a portion of the agent. In cases where the agent is cytotoxic, this delayed release can allow for the cell to function prior to release of the agent, e.g., after migration to a tumor or other disease site.

The methods and compositions disclosed herein can be performed with autologous, allogeneic, or xenogeneic cells and do not require (but can include) the use of chemical reactions or new materials or drugs.

As used herein, the term "particle" includes nanoparticles, microparticles, nanocarriers, microcarriers, polymeric particles, lipid vesicles, and the like. Nano-scale particles are considered herein to be up to 1000 nm at their largest cross-sectional dimension. Micron-scale particles are over 1.0 micron at their largest cross-sectional dimension (e.g., 1.0 micron up to 100 microns, or larger, e.g., 1.0 to 2.0 microns, 1.0 to 10.0 microns, 5 to 25 microns, and 25 to 50 microns), and can also be made according to the methods described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A is a scanning electron micrograph of PLGA particles. Scale bar: 1 μm.

FIG. 2B is a histogram depicting the representative distribution of particle diameter as determined by dynamic light scattering.

FIG. 2C is a bar graph depicting interaction/binding of cells with particles that were negatively charged, positively charged, lipid coated, or modified with a CD90 antibody. Cell-particle association was monitored at 4, 8 and 12 hours.

FIG. 2D is a bar graph depicting cell internalization of particles that were negatively charged, positively charged, lipid coated, or modified with a CD90 antibody. Particle internalization was monitored at 4, 8 and 12 hours.

FIGS. 2E-F are confocal micrographs of internalized particles stained MSCs (red) with internalized DiO loaded PLGA particles (green) on days 1 (2E) and 7 (2F) following incubation with the loaded particles. Scale bar: 10 μm.

FIG. 8A is a bar graph depicting viability of MSCs engineered with PLGA particles immediately and 48 hours after modification.

FIG. 8B is a line graph depicting proliferation of MSCs engineered with PLGA particles and unmodified MSCs.

FIG. 8C is a bar graph depicting adhesion of MSCs engineered with PLGA particles and unmodified MSCs on tissue culture plastic at 10, 30, and 90 minutes.

DETAILED DESCRIPTION

The present disclosure provides a platform cell-based technology that aims to target therapeutic, diagnostic, and/or imaging agents to specific tissues. The technology enables the delivery of high concentrations of drugs or other diagnostic or imaging agents that are associated or 'linked' to cells capable of efficiently engrafting within specific tissues. In some embodiments, cells are utilized as delivery vehicles for drug encapsulated particles. Representative applications include treatment of multiple myeloma and osteoporosis/osteogenesis imperfecta, treatment of acute and chronic lung diseases, and treatment of cancer.

Figures 1A, 1B:
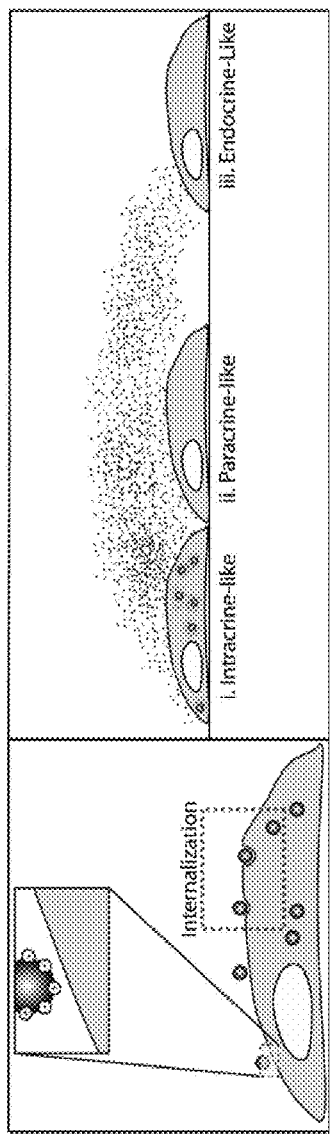
FIG. 1A is a schematic illustration depicting functionalization of cells with biodegradable particles (e.g., positively charged particles) to generate cells with internalized particles.
FIG. 1B is a schematic illustration of control of the cell and neighboring microenvironment by release of an agent encapsulated in an internalized particle. The release of the agent can control the fate of the particle carrying cell through (i) intracrine-like signaling, (ii) the neighboring cell, through paracrine-like signaling, (iii) and distant cells through endocrine-like signaling.

In some embodiments, the present disclosure provides methods to control the cellular microenvironment through simple biomaterial-based cell modification approaches independent of genetic manipulation or the presence of an artificial substrate. Readily internalized biodegradable particles containing phenotype altering agents can be used to control cell fate (FIG. 1A). Remarkably, differentiation factors released from internalized particles can promote differentiation of particle-carrying cells as well as neighboring and distant cells (FIG. 1B). This approach presents a new tool that can be easily transferred to in vitro and in vivo applications to program cell fate and the cellular microenvironment.

In some embodiments, particles that include (e.g., encapsulate) an active agent are contacted with cells (e.g., in vitro). In some embodiments, the cells are adhered or in suspension. After a period of time (e.g., 1, 2, 3, 5, 7, 9, 10, 12, 15, 17, 20 or even 24 hours or more), a substantial fraction of the particles become internalized stably within the cells. The particles biodegrade within the cells over time, releasing the active agent within the cells. However, the particles can remain within the cells, and the cells can remain intact, and in many embodiments, the cells remain viable. The cells then release the active agent into the extracellular space, where the active agent can affect the original cell (e.g., autocrine signaling), neighboring cells (e.g., paracrine signaling), and/or distant cells (e.g., endocrine-like signaling) (FIG. 1B).

Cells

Essentially any cell can be used in the methods and compositions described herein. For animal use it is preferred that the cell is of animal origin, while for human use it is preferred that the cell is a human cell; in each case an autologous cell source is preferred, although an allogeneic or xenogeneic cell source can be utilized. The cell can be a primary cell, e.g., a primary hepatocyte, a primary neuronal cell, a primary myoblast, a primary mesenchymal stem cell, primary progenitor cell, or it can be a cell of an established cell line. It is not necessary that the cell be capable of undergoing cell division; a terminally differentiated cell can be used in the methods described herein. In this context, the cell can be of any cell type including, but not limited to, epithelial, endothelial, neuronal, adipose, cardiac, skeletal muscle, fibroblast, immune cells (e.g., dendritic cells), hepatic, splenic, lung, circulating blood cells, reproductive cells, gastrointestinal, renal, bone marrow, and pancreatic cells. The cell can be a cell line, a stem cell (e.g., a mesenchymal stem cell), or a primary cell isolated from any tissue including, but not limited to brain, liver, lung, gut, stomach, fat, muscle, testes, uterus, ovary, skin, spleen, endocrine organ and bone, etc. The use of MSCs for drug delivery is reviewed in Menon et al., Stembook, ed. The Stem Cell Research Community (Jan. 15, 2009), which is incorporated herein by reference in its entirety.

Where the cell is maintained under in vitro conditions, conventional tissue culture conditions and methods can be used, and are known to those of skill in the art. Isolation and culture methods for various cells are well within the knowledge of one skilled in the art.

Functionalization of cells with particles is described, e.g., in WO 2009/134866, which is incorporated herein by reference in its entirety. If so desired, a cell can be treated prior to functionalization with a ligand and/or a particle. Cells can be pre-treated with various agents to promote expression of certain receptors on the cell surface, or to promote the cell to produce specific factors in order to enhance its homing and engraftment, or alternatively to promote a specific cell function prior to systemic delivery. For example, a cell can be induced to have enhanced cell migration prior to delivery to a subject for treatment.

In addition, both heterogeneous and homogeneous cell populations are contemplated for use with the methods and compositions described herein. In addition, aggregates of cells, cells attached to or encapsulated within particles, cells within injectable delivery vehicles such as hydrogels, and cells attached to transplantable substrates including scaffolds are contemplated for use with the methods and compositions described herein.

In some embodiments, the cells are contained within an organ, tissue, or cell aggregate (e.g., a pancreatic islet). The administration of particles to a tissue or organ ex vivo and the introduction of the tissue or organ into a subject are contemplated for use with the methods and compositions described herein.

Exemplary cells for use in the methods and compositions described herein include, without limitation, B cells, mesenchymal stem cells, hematopoetic stem cells, and dendritic cells.

Due to their unique property to migrate to specific tissues or pathological lesions, cells are unique vehicles for delivering therapeutic agents. For example, cell carriers exhibiting endogenous tumor homing activity have been recently exploited to chaperone viruses to the tumor site and for transferring exogenous genes to cancer cells (Morizono et al., 2003, Hum. Gene Ther., 14:59-66; Gomez-Navarro et al., 2000, Gene Ther., 7:43-52). Stem cells have been used to deliver genes to the tumors, especially for glioma where locally or distant delivery of neural stem and precursor cells have been shown to home to sites of glioma (Herrlinger et al., 2000, Mol. Ther., 1:347-357). Interestingly, neural stem cells genetically modified to produce the prodrug activating enzyme cytosine deaminase (CD), effected an 80% reduction in the resultant tumor mass, when tumor animals were treated with the systemic prodrug, 5-fluorocytosine (Aboody et al., 2000, Proc. Natl. Acad. Sci. USA, 97:12846-51). Mesenchymal stem cells have also been co transduced with a homing receptor (CXCR4) and with a gene that promotes osteogenesis (Cbfa-1) ameliorated glucocorticoid-induced osteoporosis by systemic transplantation of genetically manipulated MSCs (Lien et al., 2009, J. Bone Miner. Res., 24:837-848). Locally infused mesenchymal stem cells engineered to express secreted recombinant tumor necrosis factor apoptosis ligand (TRAIL) demonstrated a profound anti-tumor effect in vivo against a glioblastoma model (Sasportas et al., 2009, Proc. Natl. Acad. Sci. USA, 106: 4822-27).

There are multiple cell types that exhibit substantial homing potential to specific tissues either in their native form or following ex vivo manipulation. For example, native dendritic cells home effectively to the lymph nodes in situ. Although exogenously infused dendritic cells do not exhibit substantial homing potential, they can be engineered with particular chemokine receptors to exhibit significantly enhanced homing potential to lymphoid tissue (Garrod et al., 2006, J. Immunol., 177:863-868). In addition to dendritic cells, systemically infused hematopoietic stem cells home effectively to the bone marrow, systemically infused neural stem cells home to sites of gliomas (Brown et al., 2003, Hum. Gene Ther., 14:1777-85), and mesenchymal stem cells home preferentially to sites of injury and tumors (Karp et al., 2009, Cell Stem Cell, 4:206-216) and aside from the bone marrow, do not typically exhibit substantial long term engraftment in healthy organs (Koc et al., 1999, Exp. Hematol., 27:1675-81; Pereboeva et al., 2003, Stem Cells, 21:389-404; Studeny et al., 2004, J. Natl. Cancer Inst., 95:1593-1603). In the case of cancer, mesenchymal stem cells home to tumors, preferentially survive and proliferate in the presence of malignant cells and become incorporated into the tumor architecture as stromal fibroblasts (Pereboeva et al., 2003, Stem Cells, 21:389-404). Furthermore, it has been recently shown that systemically administered mesenchymal stem cells home to breast cancer metastasis of the lung (Studeny et al., 2004, J. Natl. Cancer Inst., 95:1593-1603).

In some embodiments, the cell expresses a protein (e.g., P-glycoprotein) that is capable of transporting an agent out of the cell. The protein can be expressed endogenously by the cell or exogenously, e.g., from an exogenous nucleic acid.

In some embodiments, the cell exports one or more agents via a multidrug transporter (e.g., P-glycoprotein). In some embodiments, the cell exports one or more agents through a gap junction. In some embodiments, the cell exports one or more agents in exosomes.

Cryopreservation of Cells

In some embodiments, the cells can be cryopreserved, e.g., after attachment and/or internalization of particles, and remain viable. As contemplated herein, the present disclosure includes the use of a variety of cryopreservation techniques and cryomedia. For example, in certain embodiments, the cryomedium can include about 1-30% (e.g., 5-10%) DMSO or glycerol and/or 10-50% serum, such as human serum. In some embodiments, the cryomedia can be serum-free. In certain embodiments, controlled rate freezing can be used, while other embodiments can include the use of insulated containers in which samples of cells mixed with cryomedia are placed in the freezer, such as at temperatures ranging from about −70° C. to −140° C. In certain embodiments, cells can be cryopreserved for 2-4 weeks at temperatures of approximately −70° C. or lower (e.g., about −80° C. or lower, about −90° C. or lower, about −100° C. or lower, about −110° C. or lower, about −120° C. or lower, about −130° C. or lower, or about −140° C. or lower). At lower temperatures, such as at about −120° C. or lower, cells can be cryopreserved for at least a year or longer. Examples of serum free media useful with the disclosed compositions and methods can include XVIVO10, XVIVO15, XVIVO20, StemPro, and other commercially available serum-free media. In some embodiments, the cryopreserved cells are stored, e.g., for about one day, about two days, about three days, about four days, about one week, about two weeks, about three weeks, about one month, about two months, about three months, about six months, about one year, or longer. Following storage, the cells can be administered to a subject.

Particles

The properties of the particles can differ between types of particles or can even differ within a single particle, for example with respect to a number of parameters including their size, morphology, composition, surface charge, porosity, surface texture, concentration of functional domains or type of domain, degradation profile, whether they contain one or more agents (including growth factors, magnets, cytokines, adhesive agents, toxins, proteins, peptides, enzymes, nucleic acid, antibodies, cell receptors, or fragments thereof), the location of such agent (e.g., on the surface or internally), etc. If so desired, the particle can be composed of an agent, such that approximately 1% to substantially the entire particle (i.e., approximately 100%) is the desired agent. In addition to containing a magnetic agent, the particle itself can be or comprise a coated or uncoated magnetic material, or a paramagnetic or superparamagnetic material.

Particles can interact with a cell surface (e.g., prior to internalization) directly through an interaction with the cell membrane. Any functionality, e.g., one or more types of functional groups, present on the particle can be, e.g., polymeric, non-polymeric or oligomeric. The binding sites on the particles can be ionic (cationic and/or anionic) or non-ionic provided that the particle can interact with the cell surface. A particle can be attached to a cell using a 'bottom-up' approach where the cell surface is pre-functionalized by various chemical and/or physical methods. In some embodiments, particles can be taken up by cells without attachment to the membrane, e.g., by pinocytosis.

The size and shape of the particles are important in determining the fate of the particles in targeting. Particles <200 nm have been demonstrated to be internalized by cells (Farokhzad et al., 2006, Expert Opin. Drug Deliv., 3:311-324). Recent studies show that rod shaped particles are not as effectively internalized compared to spherical particles (Chithrani et al., 2006, Nano Lett., 6:662-668). The properties of the material also have a great impact on internalization (Farokhzad et al. 2006, Expert Opin. Drug Deliv., 3:311-324; Win et al., 2005, Biomaterials, 26:2713-22). Moreover, positively charged particles are more readily internalized than uncharged particles. The results described herein demonstrate that larger particles (e.g., about 1-2 μm) can be internalized, e.g., without substantial exocytosis over time.

Another 'bottom-up' approach can be used wherein the cell surface is first functionalized, followed by the attachment of the linker and the functionalized particle. The choice of linker molecule would be such that one end adheres to a pre-functionalized cell and the other end attaches to a functionalized particle. The binding agent (on the pre-functionalized cell) or the linker is conjugated to a functional group on the particle. Alternatively, the particle or the linker is conjugated to a functional group of the binding agent.

Another particle-based approach is achieved using heterogeneous (e.g., janus) particles with different features. One portion, e.g., one half of a given particle can have cell adherent functionalities, which would allow the particle to interact with the cell surface (e.g., cationic polymers that interact with the cell membrane), while the other half of the particle would be designed for the desired application of the methods described herein, for example drug delivery.

Particle properties can differ from one another (e.g., a heterogeneous population) or can differ within a single particle population with respect to many parameters including, but not limited to, size, diameter, shape, composition, surface charge, degradation profile, whether they contain one or more agents, or the location of such agent (e.g., on the surface or internally).

One of the modifications of the 'heterogeneous particles' includes targeting one half the particle (which is bound to the cells) to deliver an agent and the other half is functionalized to perform a specific function including, but not limited to, applications such as directed cell migration, directed cell attachment and targeted delivery among others.

Another type of functionalization can be achieved by using material that contains two different functionalities separated by a linker molecule. One of the two functionalities specifically interacts with the cell (e.g., within the cell membrane or cytoplasm) whereas the other functionality is present in the external environment for the desired application of the methods described, for example drug delivery. The other functionality attached to the cell can be internalized through the cell membrane and can act as a sensor and/or marker for the cell or can be bound to the surface of the cell membrane by different approaches.

Another technique involves assembling polymer chains to coat the cell surface through proper interaction between the polymer chain and the cell membrane.

Functionalized (e.g., NHS, peptides, epoxy, imidoester, etc.) polymers can be used to encase the cell membrane so that the functionalized polymer interacts with the cell surface. This technique can be applied by sequential adsorptions of polymers or by emulsion techniques known to those of skill in the art.

Polymers can be sequentially applied to the cell membrane such that the polymer forms a layer over the cell membrane. In addition, functionalized particles can be adhered to the polymer layer for the desired application by e.g., sequential adsorption or by attachment of a functionalized particle to pre-adsorbed polymer on a cell surface.

The binding interaction can be physical, e.g., ionic, in a charged polymer, antibody-antigen interaction, etc. Similarly the interaction can be chemical depending on the polymer functionality (amine, carboxyl, sulphide, etc.).

Particles and/or linkers at the site of conjugation can also contain a cleavable site that is cleaved in response to a biological event or controlled externally. These particles can diffuse into tissue or remain in the vicinity of the cells.

Particles can also be used to enhance localization of transplanted (injected or implanted) cells, e.g., reactive groups attached to cells can be used to immobilize cells within or on certain tissues or materials. In addition, particles with a higher degree of elasticity (e.g., soft particles) can be used to enhance the potential of the particles to localize by transporting through biological barriers (e.g., vascular endothelium).

Properties of the particle that can be modified include, but are not limited to, shape, surface charge, porosity, chemical composition, relative hydrophobicity/hydrophilicity, mechanical properties and surface texture. A particle can be modified through attaching biological (e.g., antibodies, peptides, nucleotides) or synthetic (e.g., small molecules, aptamers) molecules. Similar techniques can also be used to control the timing or location of activity. In addition, particles can further comprise one or more agents. The agents can be located (e.g., incorporated) within the particle (e.g., within pores or channels of the particle) and/or on the external surface of the particle. In some instances, the particles are pre-loaded with one or more agents. When the particle contains a ligand, it is preferred that the ligand does not interact with the cell directly, but rather the ligand interaction occurs with the particle only.

Synthetic, natural, as well as semi-synthetic polymers, can be used for the synthesizing the polymeric particles. Different synthetic polymers include, for example, hydrogel polymers (PEG, PVA, etc.) or acrylates. These polymers can be linear or crosslinked according to the needs of one skilled in the art. Natural polymers that can be used include, but are not limited to, hyaluronic acid, gelatin, chitin, etc. For physical interactions several polymers including, for example poly ethylene imines (PEI), poly (lysine), chitosan, or cellulose can be used for charge based adhesion to the cell surface. The list of polymers that can be used includes, but is not limited to, biodegradable polymers such as poly (lactide) (PLA), poly(glycolide) (PGA), poly(lactide-co-glycolide) (PLGA), poly(caprolactone) (PCL), polycarbonates, polyamides, polyanhydrides, polyphosphazene, polyamino acids, polyortho esters, polyacetals, polycyanoacrylates and biodegradable polyurethanes; non-biodegradable polymers such as polyacrylates, ethylene-vinyl acetate polymers and other acyl-substituted cellulose acetates and derivatives thereof; polyurethanes, polystyrenes, polyvinyl chloride, polyvinyl fluoride, poly(vinyl imidazole), chlorosulphonated polyolefins, and polyethylene oxide. Examples of biodegradable natural polymers include proteins such as albumin, collagen, synthetic polyamino acids and prolamines; polysaccharides such as alginate, heparin; and other naturally occurring biodegradable polymers of sugar units. Alternately, combinations of the aforementioned polymers can be used.

Examples of inorganic particles that can be used include, but are not limited to, the following: titanium dioxide, calcium carbonate, calcium phosphate, calcium silicate, silver and gold nanoparticles, and magnetic particles, among others. Different types of particles with a wide range of geometries that are useful for the methods described herein can be used. A non limiting list of particle shapes includes, for example core-shell material, hollow particles, cage like particles, among others.

In certain embodiments the particles disclosed herein can be modified to include targeting agents that will direct the particle to a particular cell type, collection of cells, or tissue. Preferably, the targeting agents are associated with the surface of the particles. A variety of suitable targeting agents are known in the art (Cotten et al., Methods Enzym. 217: 618, 1993; Torchilin, Eur. J. Pharm. Sci. 11:881, 2000; Garnett, Adv. Drug Deliv. Rev. 53:171, 2001; Peer et al., Nat. Nanotech. 2:751, 2007). For example, any of a number of different materials that bind to antigens on the surfaces of target cells can be employed. Antibodies to target cell surface antigens will generally exhibit the necessary specificity for the target. In addition to antibodies, suitable immunoreactive fragments can also be employed, such as the Fab, Fab', or F(ab')2 fragments. Many antibody fragments suitable for use in forming the targeting mechanism are already available in the art. Similarly, ligands for any receptors on the surface of the target cells can suitably be employed as targeting agent. These include any small molecule or biomolecule, natural or synthetic, which binds specifically to a cell surface receptor, protein or glycoprotein found at the surface of the desired target cell.

There are other targeting agents, such as nucleic acid ligands, such as aptamers, which are small oligonucleotides that specifically bind to certain target molecules and are potential candidates to target proteins over-expressed in cancer cells, such as prostate cancer cells. A nucleic acid ligand is a nucleic acid that can be used to bind to a specific molecule. For example, pegaptanib is a pegylated anti-VEGF aptamer, a single stranded nucleic acid that binds with high specificity to a particular target. Although the pegaptanib aptamer was originally approved by FDA in 2004 to treat age-related macular degeneration (AMD) disease, it has the potential to treat prostate cancer because it binds specifically to VEGF165, a protein recognized as the key inducer of tumor angiogenesis. Latil et al., Int. J. Cancer, 89, 167-171 (2000) suggests that VEGF expression could be used as a prognostic marker in early-stage tumors. Specific aptamers include, for example, Aptamer O-7 which binds to osteoblasts; A10 RNA aptamer, which binds to prostate cancer cells; aptamer TTA1, which binds to breast cancer cells; and the extended A9 RNA aptamer (Javier et al., Bioconjug. Chem., 2008, 19:1309-12). See also, Wilson et al., U.S. Published Patent Application No. 20090105172. In general, aptamers are stable in a wide range of pH (~4-9), physiological conditions, and solvents. Aptamers are known to be less immunogenic than antibodies and can penetrate a tumor more easily because of size. The shape of aptamer binding sites, which includes grooves and clefts, provide highly specific characteristics and drug-like capabilities. Active targeting, however, requires that the RNA aptamers discriminate cancer cells from normal cells.

Other exemplary targeting agents include peptides, such as CLT1 and CLT2, which bind to fibrin-fibronectin complexes in blood clots. Various peptides are well known in the art for binding to cells in the brain, kidneys, lungs, skin, pancreas, intestine, uterus, adrenal gland, and prostate, including those described in Pasqualini et al., Mol. Psychiatry, 1:421-422 (1996) and Rajotte et al., J. Clin. Invest., 102:430-437 (1998), for example.

In some embodiments, the particles disclosed herein include a stealth polymer (e.g., an inert, non-degradable polymer such as PEG). See, e.g., Yokoyama et al., Cancer Research 51:3229, 1991; Gref et al., Science 263:1600, 1994; Gref et al., Advanced Drug Delivery Reviews 16:215, 1995; Klibanov et al., FEBS Lett. 268:235, 1990; VertutDoi et al., Biochimica Biophysica Acta—Biomembranes 1278: 19, 1996; and Gref et al., Colloids Surfaces B—Biointerfaces 18:301, 2000. In some embodiments, the particles disclosed herein include a targeting agent covalently bound to a stealth polymer.

In some embodiments, one or more agents is encapsulated within a particle. In some embodiments, one or more agents is covalently attached to the particle, e.g., covalently attached to a surface of the particle and/or covalently attached to a polymer chain within the particle (e.g., at an end or on the length of the polymer chain).

Active Agents

In some embodiments, the particle further includes one or more active agents, e.g., one or more therapeutic, immunomodulatory, or diagnostic agents. Exemplary active agents include biomolecules, bioactive agents, small molecules, drugs, prodrugs, proteins, polypeptides, immunogens, haptens, polynucleotides, and adjuvants.

In some embodiments, the agent is selected from analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof.

In some embodiments, the active agent enhances engraftment of a cell (e.g., a cell containing a particle or a neighboring or distant cell), promotes mobilization and/or homing of a cell (e.g., a cell containing a particle or a neighboring or distant cell), and/or promotes endogenous cell processes (e.g., production/or secretion of endogenous proteins).

In some embodiments, the active agent is selected from acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexamethasone, dexchlorpheniramine, diclofenac, dicoumarol, digoxin, dehydroepiandrosterone, dihydroergotamine, dihydrotachysterol, dirithromycin, donezepil, efavirenz, eprosartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenyloin, frovatriptan, fuirazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremitfene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

In some embodiments, the active agent is an antiproliferative or chemotherapeutic drug and is selected from Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Avastin, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cisplatin, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

In some embodiments, the agent is a DNA plasmid, a short interfering RNA (siRNA), a micro RNA (miRNA), a short hairpin RNA (shRNA), an antisense RNA, or other RNA-based therapeutic, an oligopeptide, a peptide, a monoclonal antibody, a cytokine, or other protein therapeutic.

In certain embodiments the agent comprises a growth factor or a cytokine or other factor such as leptin, sortilin, transglutaminase, prostaglandin E, 1,25-dihydroxyvitamin D3, ascorbic acid, β-glycerol phosphate, TAK-778, statins, interleukins such as IL-3 and IL-6, growth hormone, steel factor (SF), activin A (ACT), retinoic acid (RA), epidermal growth factor (EGF), bone morphogenetic proteins (BMP), platelet derived growth factor (PDGF), hepatocyte growth factor, insulin-like growth factors (IGF) I and II, hematopoietic growth factors, peptide growth factors, erythropoietin, interleukins, tumor necrosis factors, interferons, colony stimulating factors, heparin binding growth factor (HBGF), alpha or beta transforming growth factor (α or β-TGF) such as TGF-β1, fibroblast growth factors, vascular endothelium growth factor (VEGF), nerve growth factor (NGF) and muscle morphogenic factor (MMP).

In certain embodiments, the agent is a chemoattractant. In this case, release of the agent from the cell can create a chemoattractant gradient to promote activation and/or homing of at least on cell (e.g., locally or from a distance).

In some embodiments, a particle includes one or more agents that assist in the transport of another agent from inside the cell to outside the cell. For example, the particle can include a dendrimer, cell-penetrating peptide, or cationic polymer.

In some embodiments, a particle includes one or more imaging agents. Exemplary agents include quantum dots, contrast agents, iron oxides, fluorescent moieties, and/or radioisotopes.

Contrast agents can be used with various imaging modalities, such as X-rays, computerized tomography, Magnetic Resonance Imaging (MRI), nuclear imaging or ultrasound, to enable or enhance imaging. For use in MRI, for example, the particles can include any of a number of existing or novel paramagnetic nanoparticle contrast agents.

Various fluorescent moieties are known that can be incorporated into the particles disclosed herein. Fluorescent labels include near-infrared fluorophores such as Cy5, Cy5.3™, Cy5.5™, and Cy7™ fluorophores (Amersham Piscataway, N.J.), Alexa Fluor® 680, Alexa Fluor® 700, and Alexa Fluor® 750 fluorophores (Molecular Probes Eugene, Oreg.), Licor NIR™, IRDye38™, IRDye78™, and IRDye80™ fluorophores (LiCor Lincoln, Nebr.), or LaJolla Blue™ fluorophore (Diatron, Miami, Fla.), and indocyanine green and the fluorochromes disclosed in U.S. Pat. No. 6,083,875.

Radioisotopes suitable for nuclear imaging are known in the art and include, without limitation, Technetium-99m, Indium-111, and Gallium-67.

In certain embodiments, the agent does not transfect or aid in transfection of the cell.

Cell Administration

A variety of means for administering cells to subjects are known to those of skill in the art. Such methods can include systemic injection, for example i.v. injection or implantation of cells into a target site in a subject. Other methods can include intratracheal delivery, intrathecal delivery, intraosseous delivery, pulmonary delivery, buccal delivery, and oral delivery. Cells can be inserted into a delivery device which facilitates introduction by injection or implantation into the subjects. Such delivery devices can include tubes, e.g., catheters, for injecting cells and fluids into the body of a recipient subject. In one preferred embodiment, the tubes additionally have a needle, e.g., a syringe, through which the cells of the invention can be introduced into the subject at a desired location. In some embodiments, cryopreserved cells are thawed prior to administration to a subject.

As used herein, a "subject" or a "patient" refers to any mammal (e.g., a human), such as a mammal that may be susceptible to a disease. Examples include a human, a non-human primate, a cow, a horse, a pig, a sheep, a goat, a dog, a cat, or a rodent such as a mouse, a rat, a hamster, or a guinea pig. A subject can be a subject diagnosed with the disease or otherwise known to have the disease. In some embodiments, a subject can be diagnosed as, or known to be, at risk of developing a disease. In certain embodiments, a subject can be selected for treatment on the basis of a known disease in the subject. In some embodiments, a subject can be selected for treatment on the basis of a suspected disease in the subject. In some embodiments, a disease can be diagnosed by detecting a mutation associate in a biological sample (e.g., urine, sputum, whole blood, serum, stool, etc., or any combination thereof. Accordingly, a compound or composition of the invention can be administered to a subject based, at least in part, on the fact that a mutation is detected in at least one sample (e.g., biopsy sample or any other biological sample) obtained from the subject. In some embodiments, a cancer can not have been detected or located in the subject, but the presence of a mutation associated with a cancer in at least one biological sample can be sufficient to prescribe or administer one or more compositions of the invention to the subject. In some embodiments, the composition can be administered to prevent the development of a disease such as cancer. However, in some embodiments, the presence of an existing disease can be suspected, but not yet identified, and a composition of the invention can be administered to prevent further growth or development of the disease.

The cells can be prepared for delivery in a variety of different forms. For example, the cells can be suspended in a solution or gel or embedded in a support matrix when contained in such a delivery device. Cells can be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the invention can be prepared by incorporating cells as described herein in a pharmaceutically acceptable carrier or diluent and, as required, other ingredients enumerated above, followed by filtered sterilization.

It is preferred that the mode of cell administration is relatively non-invasive, for example by intravenous injection, pulmonary delivery through inhalation, oral delivery, buccal, rectal, vaginal, topical, or intranasal administration. However, the route of cell administration will depend on the tissue to be treated and can include implantation. Methods for cell delivery are known to those of skill in the art and can be extrapolated by one skilled in the art of medicine for use with the methods and compositions described herein.

Direct injection techniques for cell administration can also be used to stimulate transmigration through the entire vasculature, or to the vasculature of a particular organ, such as for example liver, or kidney or any other organ. This includes non-specific targeting of the vasculature. One can target any organ by selecting a specific injection site, such as e.g., a liver portal vein. Alternatively, the injection can be performed systemically into any vein in the body. This method is useful for enhancing stem cell numbers in aging patients. In addition, the cells can function to populate vacant stem cell niches or create new stem cells to replenish the organ, thus improving organ function. For example, cells can take up pericyte locations within the vasculature.

In some embodiments, the cells are introduced into the subject as part of a cell aggregate (e.g., a pancreatic islet), tissue, or organ, e.g., as part of an organ transplant method.

Delivery of cells can also be used to target sites of active angiogenesis. For example, delivery of endothelial progenitor cells or mesenchymal stem or progenitor cells can enhance the angiogenic response at a wound site. Targeting of angiogenesis can also be useful for using cells as a vehicle to target drugs to tumors.

If so desired, a mammal or subject can be pre-treated or co-treated with an agent. For example, an agent is administered to enhance cell targeting to a tissue (e.g., a homing factor) and can be placed at that site to encourage cells to target the desired tissue. For example, direct injection of homing factors into a tissue can be performed prior to systemic delivery of ligand-targeted cells. In some embodiments, an agent can be administered to enhance permeation of cells to modulate the release of agents from inside to outside the cell. Exemplary permeation enhancers include dendrimers, cell-penetrating peptides, and cationic polymers. In some embodiments, the cells are provided in a delivery device (e.g., an encapsulating material such as a hydrogel) and the agent is also present in the delivery device.

In some embodiments, cells are contacted with particles for a period of time (e.g., about 30 minutes, about one hour, about two hours, about three hours, about four hours, about six hours, about eight hours, or about ten hours) sufficient for the particles to adsorb to the cells prior to administration of the cells. The cells can then internalize the particles subsequent to administration.

In some embodiments, cells are contacted with particles for a period of time (e.g., about six hours, about eight hours, about ten hours, about 12 hours, about 14 hours, about 16 hours, about 18 hours, about 20 hours, about 22 hours, about 24 hours, about 30 hours, about 36 hours, about 42 hours, or about 48 hours) such that the particles become internalized prior to administration of the cells.

In some embodiments, cells with internalized particles are delivered to a subject with an external supply of at least one particle. The external particles can be internalized by the cells at a time, e.g., after the initial internalization and/or after delivery of the cells to the subject. In some embodiments, the external particles are delivered within a delivery device (e.g., an encapsulating material such as a hydrogel), which can also contain the cells.

The timing of release of the agents from the cells can be controlled, e.g., by altering the number or concentration of particles in the cells, the concentration of agents in the particles, the size of the particles, the molecular weight of the polymer, etc.

Applications

The compositions and methods disclosed herein can be used in various applications. For example, the compositions and methods can be used for treatment of disorders such as multiple myeloma, lung diseases (e.g., chronic obstructive pulmonary disease (COPD)) and for the treatment/prophylaxis of osteoporosis.

In some embodiments, the methods and compositions disclosed herein can be used to control the interaction of specific agents with cells. For example, hematopoietic stem cells can be treated with prostaglandin E2 to enhance multiple aspects of hematopoiesis (North et al., 2007, Nature, 447:1007-11). However, treatment is typically limited by exposure to cells prior to infusion. Through inclusion of agents such as PGE2 within HSCs prior to infusion, one can control the interaction of the PGE2 with the cells prior to, during and after infusion to promote a desired response.

In some embodiments, the compositions and methods disclosed herein can be used to promote hematapoiesis (e.g., myelopoiesis and/or lymphopoiesis). For example, through directly releasing (e.g. GM-CSF and/or IL-6) or triggering the release of specific agents. For example, the anti-CD44 v4 and v6 antibodies act on bone marrow macrophages to stimulate granulocyte-macrophage colony-stimulating factor (GM-CSF) production (v4 and v6) and interleukin-6 (IL-6) production (v6) (Khaldoyanidi et al., 2002, Blood, 99:3955-61). Another example could include delivery of Thrombopoietin to promote Megakaryocytopoiesis.

In some embodiments, the methods and compositions disclosed herein can be used to target specific tumor cells and complements in the tumor microenvironment. The compositions and methods can be used to interrupt communications via secreted factors, thereby modulating cellular growth and cancer progression. Examples include macrophage cells infiltrating pancreatic, mammary and lung tumors, which produce high levels of the proteases cathepsin B and S (Cts B and S).

In some embodiments, the methods and compositions disclosed herein can be used for targeting of stem cells or stem-cell like cells that are originators of disease processes or disease resistance, e.g., Lmo2 in T-cell acute lymphoblastic leukemia (rare form of leukemia in older children and adolescents) where Lmo2 gene recovers rapidly after radiation therapy with a 20% patient relapse rate.

In some embodiments, the methods and compositions disclosed herein can be used to enhance engraftment of hematopoietic stem cells, e.g., those derived from the bone marrow or from cord/placenta blood. An agent can be used to transiently inhibit Lnk or Lnk-mediated pathways to augment engraftment of HSCs/HPCs (Takizawa et al., 2006, Blood, 107:2968-75).

In some embodiments, the methods and compositions disclosed herein can be used to enhance the regenerative phenotype of cells. For example, cells can be loaded with agents that upregulate specific secreted frizzled-related proteins (see Alfaro et al., 2008, Proc. Natl. Acad. Sci. USA, 105:18366-71).

In some embodiments, the methods and compositions disclosed herein can be used to control cell fate in vivo. For example, the particles within cells can release factors to promote motility and/or program cells (Zhao and Karp, 2009, Chembiochem, 10:2308-10).

In some embodiments, the cells are phagocytocic cells, such as antigen presenting cells (e.g., dendritic cells) or T-cells, and the agent is an antigen or nucleic acid encoding an antigen.

In some embodiments, the compositions and methods disclosed herein can be used to promote proliferation and/or differentiation of cells after cells have been exogenously delivered. In such embodiments, the cells can contain particles encapsulating an agent that promotes proliferation and/or differentiation.

In some embodiments, the agent is erythropoietin, and the methods and compositions disclosed herein can be used in the treatment of conditions and disorders for which erythropoietin can be useful, e.g., chronic renal failure and anemia (e.g., anemia in cancers).

In some embodiments, the compositions and methods disclosed herein can be used to control the expansion and/or differentiation of cells (e.g., in vitro). For example, in an in vitro method, the cells can contain internalized particles that include modulators of cell expansion and/or differentiation. By doing so, the concentration of such agents in the medium can potentially be reduced.

In some embodiments, the compositions and methods disclosed herein can be used to enhance a cosmetic outcome, e.g., by use of an agent that can enhance production of an extracellular matrix protein (e.g., collagen), e.g., within a specific tissue.

In some embodiments, the compositions and methods disclosed herein can be used to promote long-term expression of microvilli on the surface of a cell, e.g., a cell that contains an internalized particle.

In some embodiments, the compositions and methods disclosed herein can be used to inhibit inflammatory signaling, e.g., by TNFα or other inflammatory cytokines.

In some embodiments, the compositions and methods disclosed herein can be used to deliver antibodies or other agents to inhibit bioterrorism or other infectious or harmful agents, such as viruses or bacterial toxins. These methods can be used, e.g., against Venezuelan equine encephalitis virus (VEEV), influenza viruses (e.g., avian flu, swine flu), ebola virus, severe acute respiratory syndrome (SARS) coronavirus, malarial plasmodia, and *Bacillus anthracis*.

In some embodiments, the compositions and methods disclosed herein can be used to control pain (e.g., local or systemic pain).

In some embodiments, the compositions and methods disclosed herein can be used to deliver agents across the blood-brain barrier.

In some embodiments, the compositions and methods disclosed herein can be used to enhance beta cell therapy.

EXAMPLES

Example 1. Engineering MSCs with PLGA Particles

Although MSCs readily internalize nano-sized particles (Chung et al., 2007, Biomaterials, 28:2959-66), small particles (<1 μm) that are typically endocytosed (Gao et al., 2005, Proc. Natl. Acad. Sci. USA, 102:9469-74) have been shown in other cell types to be rapidly exocytosed unless they are conjugated to the cell membrane (Panyam et al., 2003, Pharm. Res., 20:212-220; Sahoo et al., 2005, Mol. Pharm., 2:373-383; Jin et al., 2009, ACS Nano, 3:149-158; Chithrani et al., 2007, Nano Lett., 27:1542-50). To reduce the potential for exocytosis, PLGA particles with a diameter of 1-2 μm were fabricated. Rhodamine 6G dye (Sigma) or the osteogenic differentiation agent, dexamethasone (DEX), was encapsulated in poly (lactic-co-glycolic) acid (PLGA) particles using a single emulsion encapsulation technique. Briefly, 100 mg of 50:50 PLGA (carboxylic acid end group) was dissolved in 2 mL dichloromethane. DEX or dye was then added to the PLGA solution and mixed thoroughly. For complete dissolution of DEX, 10% methanol was added to dichloromethane. The PLGA solution was then added to 20 mL of 1% (w/v) polyvinylalcohol solution in deionized water and emulsified using a sonicator at 30 W for 60 seconds. The solution was then stirred overnight at room temperature on a magnetic stirrer to allow extraction and evaporation of the organic solvent. The remaining solution was centrifuged and rinsed with PBS to isolate particles and lyophilized. Particle size was determined by dynamic light scattering and confirmed by scanning electron microscopy (FIGS. 2A-B). To determine the encapsulation efficiency, briefly, 10 mg of DEX-PLGA particle was dissolved in anhydrous dimethylsulfoxide (DMSO) followed by quantification of DEX with a UV-vis spectrophotometer at 251 nm. Blank PLGA particles without any DEX served as control. DEX was reliably encapsulated in DEX-PLGA particles with an efficiency of 71±13.5% (e.g., from an initial 10 mg of DEX, ~7.1±1.35 mg was typically entrapped within the PLGA particles).

Primary human MSCs were derived from healthy consenting donors and thoroughly characterized as previously described (Colter et al., 2000, Proc. Natl. Acad. Sci. USA, 97:3213-18). MSCs were maintained in α-MEM expansion media (Invitrogen) supplemented with 15% Fetal Bovine Serum (Atlanta Biologicals), 1% (v/v) L-Glutamine (Invitrogen), and 1% penicillin:streptomycin solution (Invitrogen). Cells were cultured to 70-80% confluence before passaging. All experiments were performed using MSCs at passage number 3-6 where cells expressed high levels of MSC markers CD90 and CD29 (>99% cells), and did not express hematopoietic markers CD34 or CD45 (0% of cells) as observed from flow cytometry analysis. To improve particle uptake, PLGA microparticles were incubated with 50 μg/mL poly-L-lysine for 3 hours before incubation with MSCs. PLGA particle suspensions with concentrations of 0.1 mg/mL and 0.5 mg/mL in PBS were added to 90% confluent layers of MSCs in a 24-well plate for 10 minutes, after which the PBS was removed and complete media was added. The MSCs were allowed to internalize particles for 24 hours at 37° C.

To characterize particle internalization and stability of internalized particles, MSCs were loaded with DiO containing PLGA particles and characterized with a Zeiss LSM510 laser scanning confocal microscope equipped with a 63× water dipping objective. After a 24 hour incubation, the cells were fixed with 3.7% formaldehyde at room temperature and stained with 5 μg/mL of propidium iodide (PI) solution or 5 μl/mL DiL vybrant cell stain solution for 10 minutes to visualize the cells. The cells were visible through the red fluorescence channel and the particles were visible through the green fluorescence channel. The PLGA particles were found to be internalized by MSCs irrespective of the surface chemistry, likely via phagocytosis (Gao et al., 2005, Proc. Natl. Acad. Sci. USA, 102:9469-74) (FIGS. 2A & B). However, the kinetics of internalization was increased by modifying the surface with a positive charge or with an antibody directed towards an MSC surface antigen (e.g., CD90) (FIG. 2C). Thus positively charged particles were selected for further experimentation. Confocal microscopy demonstrated that ~95% of the PLGA particles were internalized following a 12 hour incubation (FIG. 2D).

Figure 7D:
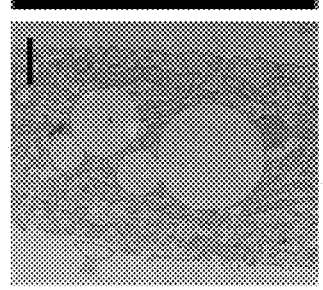
FIGS. 7B-D are a set of confocal micrographs depicting three 3D projections of a single confocal z-stack reveals showing PLGA particles (green) internalized by MSCs after 24 hours incubation. Scale bar: 10 μm.
Figure 7C:
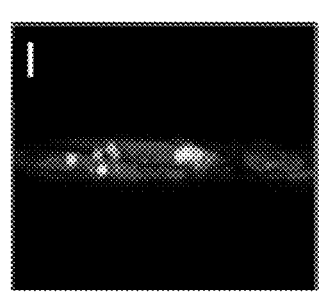
Figure 7B:
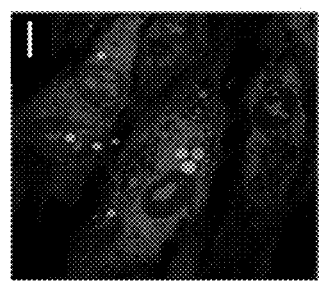
Figure 7A:
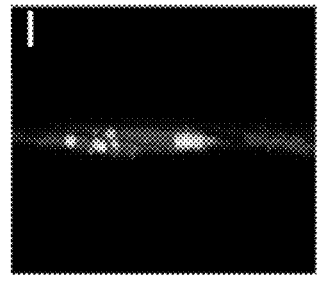
FIG. 7A is a transmission electron micrograph of MSCs with internalized MSCs polydisperse DiO loaded PLGA particles after 24 hours incubation. PLGA particles were observed in the intracellular space next to the rough endoplasmic reticulum. Scale bar: 500 nm.

Additionally, internalization of particles was confirmed with transmission electron microscopy (FIG. 7A). For transmission electron microscopy, particle modified cells were prepared as described above and fixed and analyzed. Specifically, the cells were fixed in 2.5% glutaraldehyde, 3% paraformaldehyde with 5% sucrose in 0.1 M sodium cacodylate buffer (pH 7.4), pelleted, and post fixed in 1% $OsO_4$ in veronal-acetate buffer. The cell pellet was stained in block overnight with 0.5% uranyl acetate in veronal-acetate buffer (pH 6.0), then dehydrated and embedded in Spurrs resin. Sections were cut on a Reichert Ultracut E microtome with a Diatome diamond knife at a thickness setting of 50 nm, and stained with uranyl acetate and lead citrate. The sections were examined using a FEI Tecnai spirit at 80 KV and photographed with an AMT CCD camera.

Figure 9:
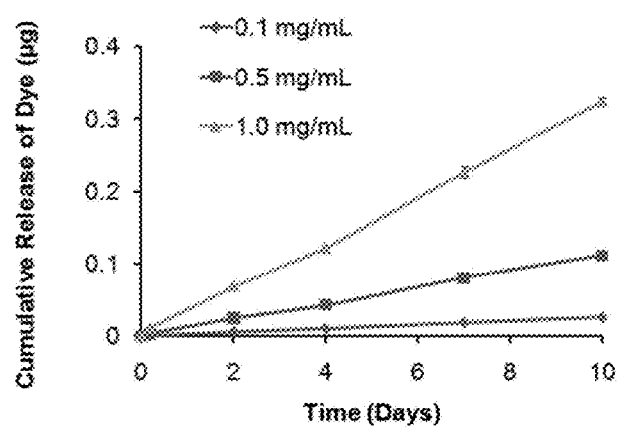
FIG. 9 is a line graph depicting release of rhodamine dye from MSCs modified with 200 μl of 0.1 mg/ml, 0.5 mg/ml, and 1.0 mg/ml rhodamine-PLGA particles into surrounding media at 37° C. over 10 days.

Importantly, in contrast to previous reports of nanoparticle exocytosis, the 1-2 μm particles were found to be stable inside the cell for at least 7 days (FIGS. 2E & F). Furthermore, modification of MSCs with PLGA particles did not impact cell phenotype including viability (FIG. 8A), adhesion (FIG. 8B), proliferation (FIG. 8C) and multilineage differentiation potential (FIG. 9). The viability, adhesion kinetics and proliferation of particle-modified MSCs and unmodified MSCs were examined using our previously reported experimental methodology (Sarkar et al., 2008, Bioconjug. Chem., 19:2105-09). Briefly, the viability of the cells was examined immediately after modification (time 0) and after the cells were incubated within 6-well plates for 48 hours using a trypan blue exclusion assay. Cell adhesion kinetics were quantified by measuring the number of adherent cells on the tissue culture surface after 10, 30, and 90 minutes. Proliferation of modified and unmodified MSCs was quantified by plating cells in T25 flasks at low density and counting the number of cells in the flask for an 8 day period with light microscopy at 10× for ten random fields. Multi-lineage differentiation potential of the particle modified MSCs and unmodified MSCs was examined by incubating cells with osteogenic and adipogenic induction media followed by respective colorimetric staining (Sarkar et al., 2008, Bioconjug. Chem., 19:2105-09). Cells were assayed for osteogenic differentiation and adipogenic differentiation using cell membrane associated alkaline phosphatase (ALP) activity and Oil Red O (ORO) staining, respectively. Particle modified MSCs cultured in respective differentiation media showed positive staining for both ORO and ALP. Particle modified MSCs cultured in expansion media, without differentiation factors, showed no ORO or ALP staining.

Figure 3A:
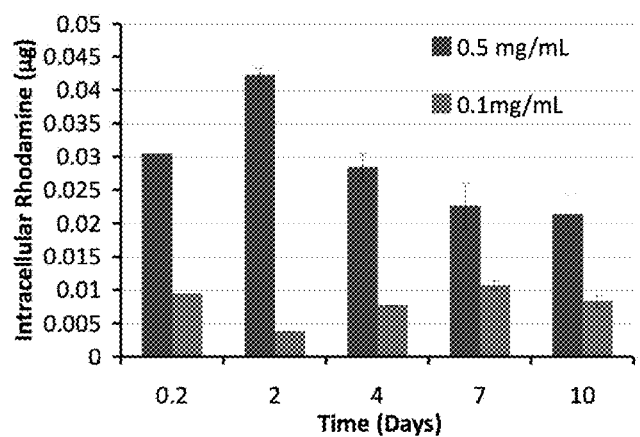
FIG. 3A is a bar graph depicting intracellular accumulation of rhodamine over time in MSCs loaded with 0.1 mg/ml or 0.5 mg/ml of rhodamine-PLGA particles. The cells were permeabilized with 5 μg/ml of L-lysine at 4 hours, 2 days, 4 days, 7 days, or 10 days, the permeabilized cells were discarded, and the dye concentration in the lysate was assessed with UV spectrophotometry.
Figure 3B:
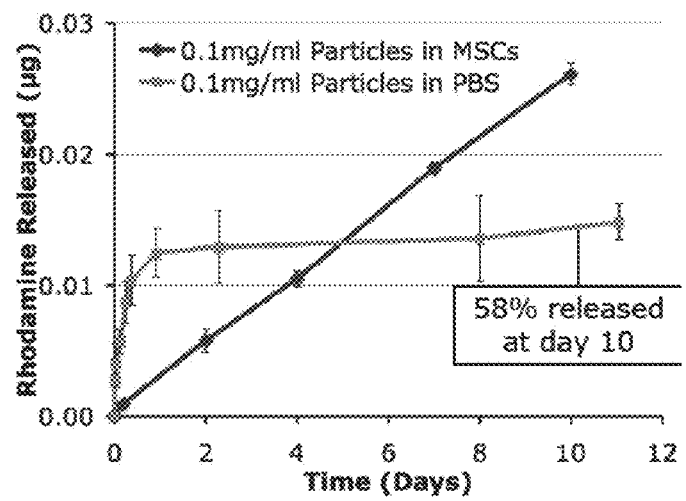
FIG. 3B is a line graph depicting kinetics of rhodamine dye from MSCs with 0.1 mg/ml internalized particles versus a suspension of 0.1 mg/ml PLGA particles without cells.

Following the development of particles that were readily and stably internalized by MSCs, we sought to examine the potential for agents encapsulated within the particles to be released into the intracellular and extracellular milieu using rhodamine dye as a model small molecule (mol. wt. 479). Intracellular accumulation of rhodamine dye was examined over a 10 day period through permeabilization of the cells at different time points following rinsing to remove residual culture media. 0.1 mg/ml, 0.5 mg/ml, or 1 mg/ml PLGA microparticles with entrapped rhodamine dye were incubated with MSCs for 24 hours at 37° C. The media was then discarded and the cells were rinsed with PBS and supplied fresh media to create a baseline for the dye release measurements. On days 2, 4, 7, 10 media was collected and the quantity of dye released was measured using a fluorescence spectrophotometer with excitation and emission wavelengths of 540 and 625 nm, respectively. Dye was released in an initial burst within the first 2 days followed by relatively constant release (FIG. 3A). To examine the potential for rhodamine to be transported into the extracellular milieu, we sampled the media throughout the culture period with a fluorescence spectrophotometer and compared this result to a particle suspension without cells. Remarkably, we detected increasing concentrations of rhodamine overtime in the culture media indicating transport from the intracellular to the extracellular milieu. Release of rhodamine from particles without cells showed a characteristic initial burst release with over 40% of encapsulated rhodamine being released within the first day followed by steady sustained release (FIG. 3B). In contrast, rhodamine was released from internalized PLGA depots at a constant rate, with 40% of entrapped rhodamine released by day 5 and 100% by day 10 (FIG. 3B). Importantly the rate of rhodamine delivery was easily tuned by changing the concentration of particles added to the cultures (FIG. 9). This demonstrates the potential of engineering cells with particles to achieve sustained targeted release of membrane permeable agents to the carrier cell and its microenvironment.

Example 2. Controlling the Fate of Particle Engineered Cells and Other Cells

Figure 4A:
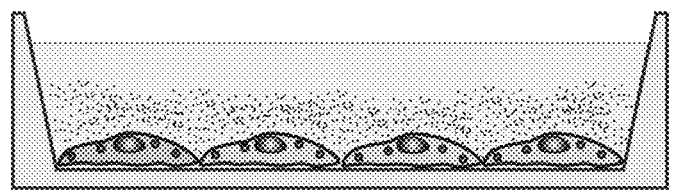
FIG. 4A is a schematic illustration of DEX release into culture media from adherent MSCs modified with DEX-PLGA particles.
Figure 4B:
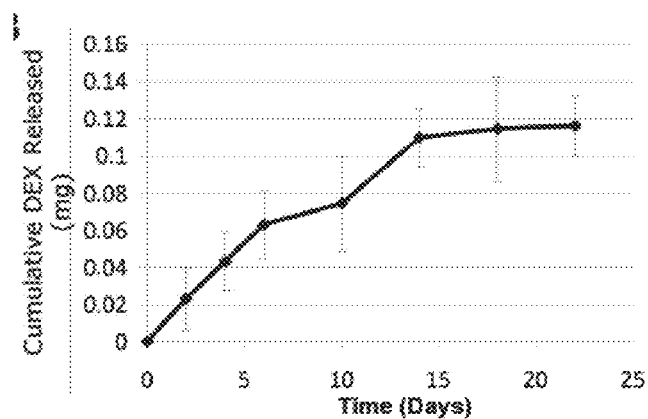
FIG. 4B is a line graph depicting release kinetics of DEX from MSCs containing DEX-PLGA particles into media at 37° C. over 21 days.

MSCs are multipotent cells capable of self renewal that can give rise to a number of unique, differentiated mesenchymal cell types including osteoblasts, chondrocytes, and adipocytes. To examine the potential to control MSC phenotype we utilized an osteogenesis assay where differentiation of MSCs to osteoblasts can easily be detected through the characteristic expression of alkaline phosphatase (ALP) (Maniatopoulos et al., 1988, Cell Tissue Res., 254:317-330). MSCs differentiate into osteogenic cells in the presence of the glucocorticoid, dexamethasone (DEX) that passively diffuses across the cell membrane (Thompson et al., 1974, Metabolism, 23:159-202; Grigoriadis et al., 1988, J. Cell Biol., 106:2139-51), but only produce mineralized extracellular matrix in the presence of ascorbic acid (A) and phosphate ions (e.g., from β-glycerol-phosphate (G)) (Maniatopoulos et al., 1988, Cell Tissue Res., 254:317-330). Instead of placing DEX into media, we incorporated DEX into PLGA microparticles that were internalized by MSCs (FIG. 4A). To quantify the amount of dexamethasone released, MSCs were incubated with 0.1 mg/ml DEX-PLGA particles for 24 hours at 37° C. On days 2, 4, 6, 10, 14, 18, and 22, 1 ml of media was collected and replenished with fresh media. The released DEX was determined using ultraviolet (UV) spectrophotometer at 251 nm. Cells with no particles and cells with blank particles (no DEX) served as controls. Quantification of dexamethasone in media above modified cells demonstrated that DEX was transported from the particle engineered MSCs to the extracellular environment for up to 2 weeks. (FIG. 4B).

Figure 4C:
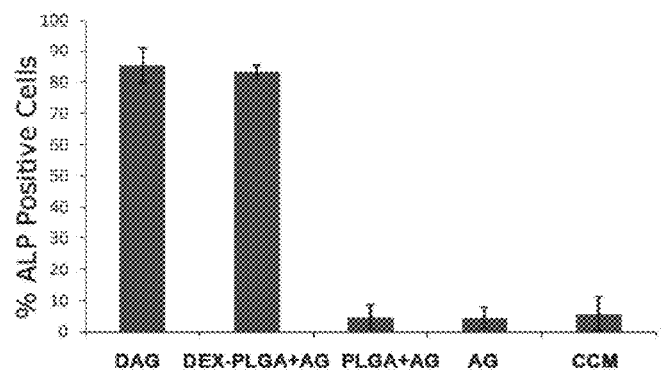
FIG. 4C is a bar graph depicting alkaline phosphatase staining (indicating osteogenic differentiation) of DEX- PLGA modified MSCs and controls. D, dexamethasone; G, β-glycerolphsophate; A, ascorbic acid; CCM, hMSC expansion media.

The media was supplemented with β-glycerolphosphate (G) and Ascorbic Acid (A) and after 21 days, osteogenic differentiation was detected via ALP staining. To evaluate osteogenic differentiation, cell membrane associated ALP activity was examined by aspirating the culture media and rinsing the cells followed by fixation with 3.7% formaldehyde solution for 10 minutes at room temperature and rinsing. After 45 minutes incubation in 0.06% Red Violet LB salt solution in Tris HCl, DMF and Naphthol AS MX-PO4, the wells were rinsed 3 times with distilled water and visualized with light microscopy. Osteogenic differentiation was identified by red staining for alkaline phosphatase. To visualize individual cells, the nuclei of the cells were stained with 100 µL of DAPI solution (1 µg/mL in PBS) after treatment with 100 µL of 0.1% TRITON X solution in PBS. To quantify the percentage of MSCs stained positively for alkaline phosphatase, ImageJ® software was used. MSCs with blank particles, and MSCs in the presence of A and G alone did not stain positive for ALP (FIG. 4C). Approximately 80% of the MSCs engineered with DEX containing particles in the presence of A and G stained positive for ALP, which was comparable to the ALP staining of MSCs (without particles) in complete osteogenic media.

Figure 4D:
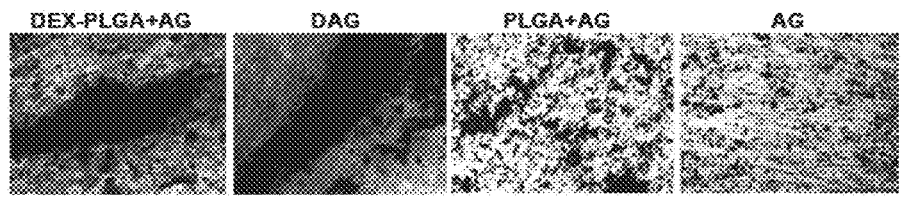
FIG. 4D is a set of micrographs of bone nodules were identified via positive dual staining for Von Kossa and ALP in DEX and internalized DEX-PLGA particle containing cultures supplemented with A and G but not in the absence of DEX or DEX-PLGA particles.

In addition, co-staining cultures with ALP and Von Kossa revealed the formation of bone nodules in DEX-PLGA cultures (FIG. 4D). The cultures stained for ALP were further examined for the presence of mineralization via the Von Kossa stain. Briefly, plates were rinsed 3-4 times in ddH$_2$O, and stained with 2.5% silver nitrate for 30 minutes. After rinsing 3-4 times in ddH$_2$O, plates were incubated in sodium carbonate formaldehyde for 1-2 minutes, rinsed, air dried, and examined by light microscopy. Since DEX binds to intracellular glucocorticoid receptors (Thompson et al., 1974, Metabolism, 23:159-202; Grigoriadis et al., 1988, J. Cell Biol., 106:2139-51), these results demonstrate that DEX released from PLGA microparticles induced osteogenic differentiation of particle modified MSCs. Thus microparticles, which do not readily undergo exocytosis, can be used to deliver phenotype altering agents such as dexamethasone to intracellularly control the fate of particle modified cells.

Figure 5A:
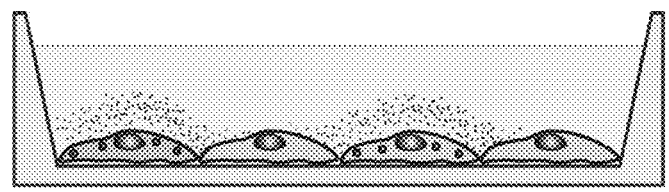
FIG. 5A is a schematic illustration of DEX-PLGA modified MSCs controlling the fate of neighboring MSCs without particles (black arrows).
Figure 5B:
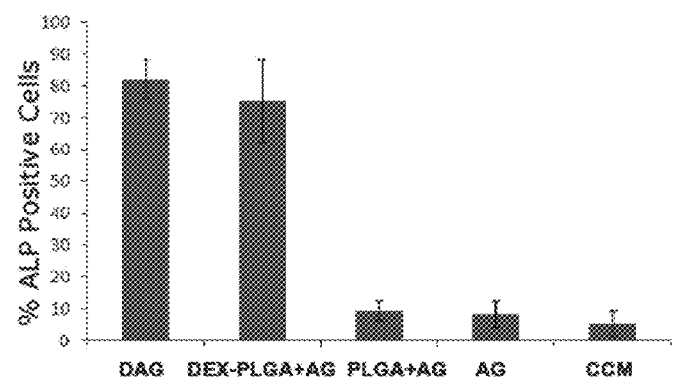
FIG. 5B is a bar graph depicting alkaline phosphatase staining (indicating osteogenic differentiation) of DEX-PLGA modified MSCs and neighboring MSCs seeded in a 1:1 ratio.

Given that DEX can be transported across the MSC membrane into the extracellular environment following internalization of DEX loaded microparticles, we envisioned particle engineered cells could be used to control the phenotype of neighboring cells in a paracrine-like manner. For an in vitro model, the previous experiment was repeated, with only half of the MSCs containing DEX-PLGA particles (FIG. 5A). Specifically, MSCs and DEX-PLGA modified MSCs were mixed in a 1:1 ratio and plated in a 6-well plate. Strikingly, following differentiation conditions, the majority of cells within the co-culture with DEX-PLGA particles stained positive for ALP (FIG. 5B). Given that cell adhesion and proliferation properties of the PLGA modified and unmodified cells were similar (FIG. S2), these Results are Likely not Due to differences in adhesion and proliferation between the two populations of cells. Thus, this data suggests that DEX released from particle modified MSCs can control the fate of adjacent cells.

Figure 6A:
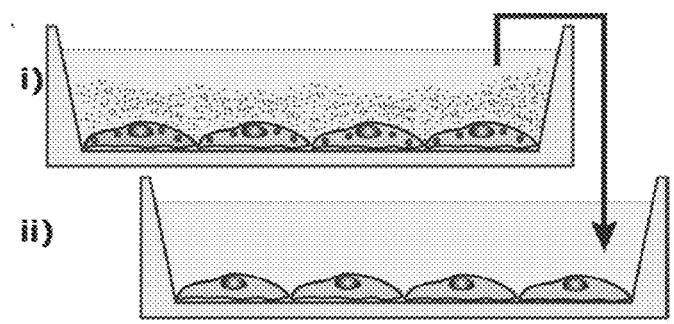
FIG. 6A is a schematic illustration of programming cell fate of distant cells (without particles) by transferring conditioned media from well i, containing DEX-PLGA modified MSCs, differentiated MSCs, or DEX-PLGA modified fibroblasts to well ii.
Figure 6B:
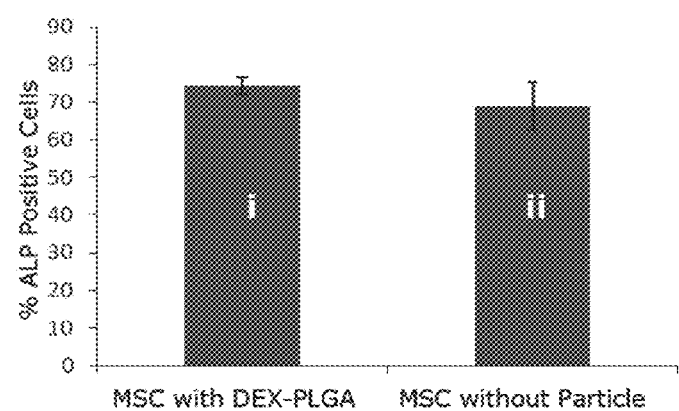
FIG. 6B is a bar graph depicting alkaline phosphatase staining (indicating osteogenic differentiation) of DEX-PLGA modified MSCs and distant MSCs treated with conditioned medium from DEX-PLGA modified MSCs.

Next we examined the potential for extracellular release of DEX from particle modified cells to promote differentiation of unmodified MSCs in a different culture dish (endocrine-like signaling). On every third day, conditioned media was transferred from particle modified cells (supplemented with G and A) to the unmodified cells and after 21 days stained to detect ALP activity (FIG. 6A). ALP staining of the unmodified cells incubated in conditioned media from DEX-PLGA modified cells was comparable to the DEX-PLGA modified MSCs (FIG. 6B). Importantly, no detectable ALP staining was observed when the media was transferred from MSCs engineered with blank PLGA particles (supplemented with G and A) and from unmodified MSCs (supplemented with G and A) to a separate dish containing unmodified MSCs.

Figure 6C:
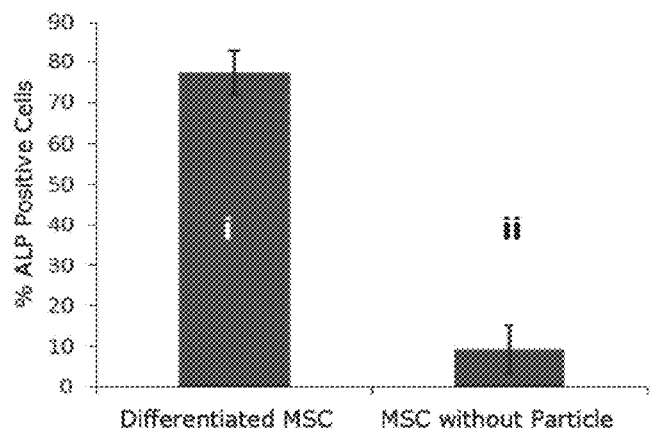
FIG. 6C is a bar graph depicting alkaline phosphatase staining (indicating osteogenic differentiation) of differentiated MSCs without DEX-PLGA particles and distant MSCs treated with conditioned media from differentiated MSCs without DEX-PLGA particles.
Figure 6D:
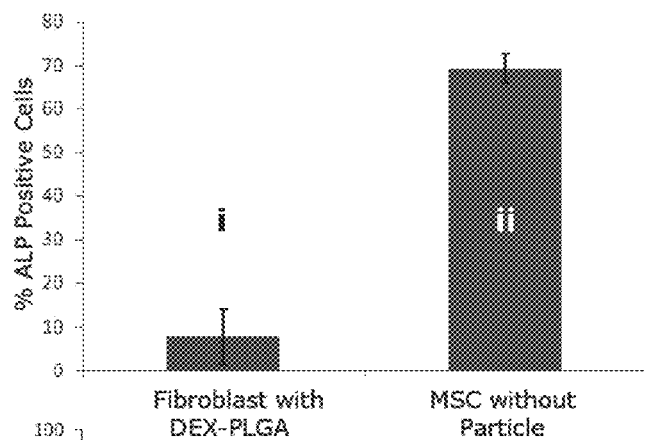
FIG. 6D is a bar graph depicting alkaline phosphatase staining (indicating osteogenic differentiation) of DEX-PLGA modified fibroblasts and MSCs treated with conditioned media from DEX-PLGA modified fibroblasts.

To ensure that the released DEX was responsible for induction of osteogenic differentiation and that this was not due to a factor released from the differentiating MSCs, additional experiments were performed. Specifically, media transferred from unmodified MSC cultures following 21 days of osteogenic differentiation (supplemented with DEX, G, and A) resulted in no detectable ALP staining (FIG. 6C). In a separate experiment, lung microvascular fibroblasts with internalized DEX-PLGA particles were used in place of MSCs. Media transferred from the DEX-PLGA modified fibroblast cultures to unmodified MSCs (supplemented with G and A) induced osteogenic differentiation of the MSCs to the same degree as media transferred from DEX-PLGA modified MSCs (FIG. 6D). These two controls demonstrate that the DEX released from the particle modified cells was responsible for inducing osteogenic differentiation of the unmodified MSCs in a different culture dish in an endocrine-like manner.

Figure 6E:
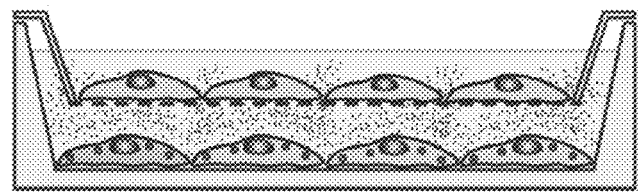
FIG. 6E is a schematic illustration DEX-PLGA modified MSCs controlling the fate of MSCs (without particles) separated by a transwell membrane.
Figure 6F:
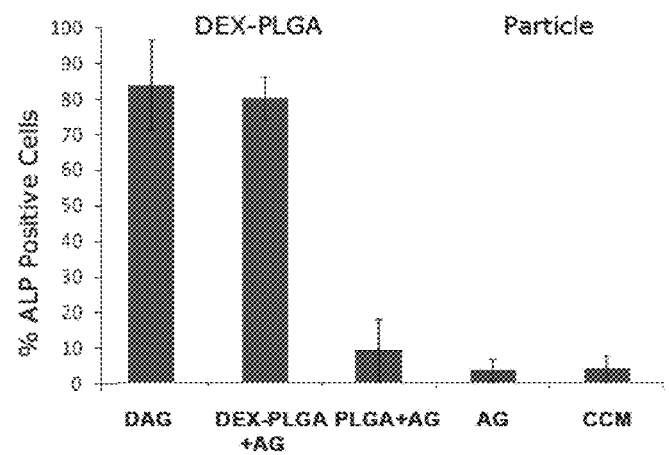
FIG. 6F is a bar graph depicting alkaline phosphatase staining (indicating osteogenic differentiation) of unmodified MSCs atop transwell membrane. D, dexamethasone; G, β-glycerolphosphate; A, ascorbic acid; CCM, hMSC expansion media.

To determine if engineered endocrine-like signaling could promote differentiation in a more relevant assay, the ability of adhered DEX-PLGA modified MSCs to impact the fate of cells on a distant transwell membrane in the same culture environment was investigated. MSCs were incubated with DEX-PLGA particles on the bottom surface of a transwell dish, and unmodified MSCs on a filter surface that was 2 mm above in the presence of A and G (FIG. 6E). Cells were stained to detect ALP activity after 21 days in culture. DEX-PLGA modified MSCs were shown to induce the differentiation of ~80% of the unmodified MSCs on the transwell membrane (FIG. 6F). This demonstrates that agents released from particle modified cells can impact the fate of distant cells without cell contact.

Example 3. Controlling Cell Fate after Cryopreservation

Figure 10A:
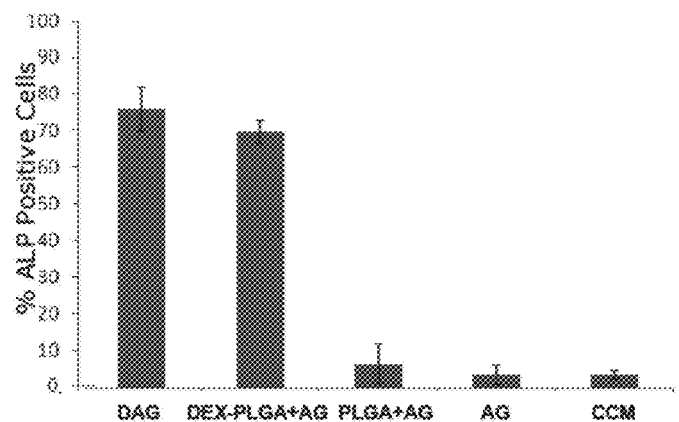
FIG. 10A is a bar graph depicting alkaline phosphatase staining of cryopreserved DEX-PLGA modified MSCs.
Figure 10B:
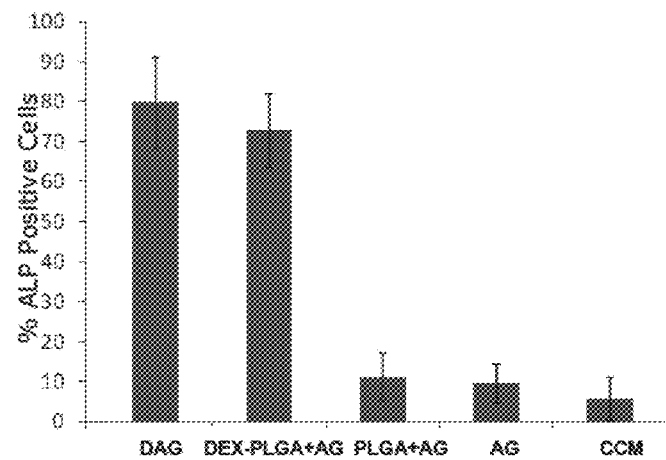
FIG. 10B is a bar graph depicting alkaline phosphatase staining of unmodified MSCs atop transwell membrane above cryopreserved DEX-PLGA modified MSCs.

To assess the potential for particle modified MSCs to retain their DEX releasing properties following cryopreservation, cells containing DEX-PLGA particles were stored for 10 days at −140° C. The DEX-PLGA particles were incubated with MSCs for 24 hours followed by trypsinization with 1× trypsin-EDTA solution. The particle modified cells were frozen in complete cell culture media supplemented with 5% dimethyl sulfoxide at −140° C. After 10 days the cells were thawed and plated. The particle modified MSCs differentiated into osteogenic cells via intracellular release of DEX, as indicated by positive alkaline phosphatase staining (FIG. 10A) and induced osteogenic differentiation of distant unmodified MSCs, comparable to non-cryopreserved DEX-PLGA modified cells (FIG. 10B). Thus, particle engineered MSCs can be cryopreserved without loss of activity.

Example 4. Cell-Based Delivery of Chemotherapeutic Agents

Figure 11A:
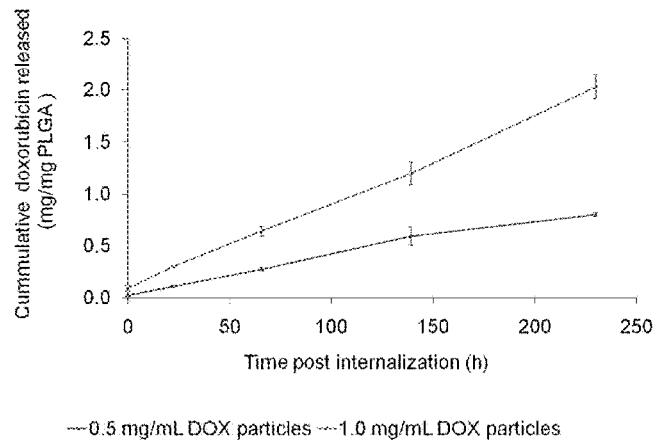
FIG. 11A is a line graph depicting release kinetics of DOX from MSCs containing DOX-PLGA particles into media at 37° C. over 10 days.

PLGA microparticles encapsulating doxorubicin (DOX) were prepared essentially as described in Example 1. 0.5 mg/ml and 1 mg/ml DOX-PLGA microparticles with entrapped doxorubicin were incubated with MSCs for 24 hours at 37° C. The media was then discarded and the cells were rinsed with PBS and supplied fresh media. On days 3, 6, and 10, the media was collected and the quantity of doxorubicin released was measured. The amount of doxorubicin released was generally linear over time and dependent on the dose of particles internalized (FIG. 11A).

Figure 11B:
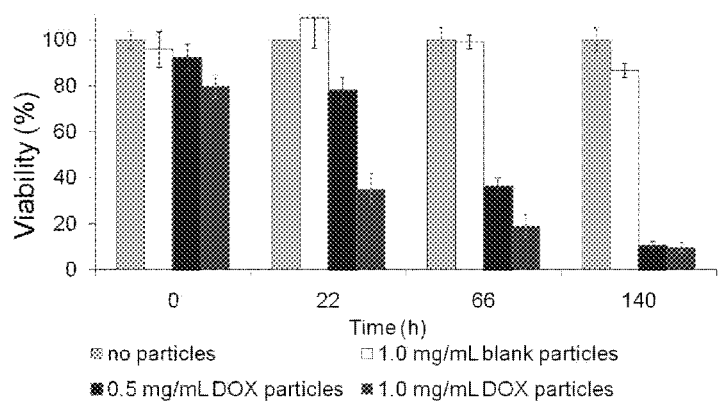
FIG. 11B is a bar graph depicting viability of F10 melanoma cells exposed to conditioned medium from MSCs without microparticles (no particles), MSCs with internalized PLGA microparticles not encapsulating DOX (1.0 mg/ml blank particles), and MSCs with internalized DOX-PLGA microparticles (0.5 mg/ml DOX particles and 1.0 mg/ml DOX particles).

Next we examined the potential for extracellular release of DOX from particle modified cells to effect F10 melanoma cells in a different culture dish. On every third day, conditioned media was transferred from particle modified MSCs to the F10 cells, and viability was measured at days 22, 66, and 140. A decrease in F10 cell viability was observed in cells loaded with DOX-PLGA, and this effect was relatively dose-dependent (FIG. 11B). This observation indicates that the released doxorubicin can act as chemotherapeutic agent to the cancer cells at a distant site.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of delivering at least one active agent to a target, the method comprising:
   providing an isolated cell comprising a particle within the cell, wherein the particle is associated with at least one active agent and comprising a polymer and having a size of about 500 nm to 5 µm; and
   contacting the target with the isolated cell,
   wherein the at least one active agent is released from the cell independently of the particle, thereby delivering the active agent to the target.

2. The method of claim 1, wherein the particle is formulated to release the at least one active agent into the cell in a controlled or predictable manner.

3. The method of claim 1, wherein the particle is formulated for delayed release of the at least one active agent over a period of at least 1, 3, 5, 7, or 10 days.

4. The method of claim 1, wherein the particle is formulated to release the at least one active agent into the extracellular environment.

5. The method of claim 1, wherein the release of the at least one active agent does not require an external stimulus or does not require cell death.

6. The method of claim 1 wherein the at least one active agent is released by degradation/dissolution/erosion/swelling of the particle, desorption/dissociation of the at least one active agent from the particle, diffusion of the at least one active agent away from the particle, or through absorption of energy.

7. The method of claim 1, wherein the at least one active agent is a therapeutic agent.

8. The method of claim 7, wherein the therapeutic agent is a drug, protein, enzyme, gene, nucleic acid, RNAi, or biomolecule.

9. The method of claim 1, wherein the at least one active agent is covalently attached to the particle.

10. The method of claim 1, wherein the at least one active agent is noncovalently entrapped in the particle.

11. The method of claim 1, wherein the isolated cell is a stem cell or a progenitor cell.

12. The method of claim 11, wherein the stem cell is a mesenchymal stem cell.

13. The method of claim 1, wherein the isolated cell is viable.

14. The method of claim 1, wherein the target is a region within a subject.

15. The method of claim 14, wherein contacting comprises injecting or implanting the isolated cell into the subject.

16. The method of claim 1, wherein the method is used to treat, diagnose, or image osteoporosis, cancer, inflammatory disease, Parkinson's disease, diabetes, vascular disease, heart disease, kidney disease, liver disease, infection, sepsis, anemia, thyroid disease, blood disorders, ischemic tissues, gastrointestinal disease, skin disease, lung disease, or is used for a prophylaxis or is used as a vaccine or to promote tolerance.

17. The method of claim 15, wherein the target is a distant site from the location of injection or implantation.

18. The method of claim 14, wherein the method comprises extravasating of the isolated cell with the particle through an endothelial layer.

19. The method of claim 1, wherein the isolated cell has been cryopreserved prior to the step of contacting the target with the isolated cell.

20. The method of claim 1, wherein the polymer is poly(lactide-co-glycolide).

* * * * *

UNITED STATES PATENT AND TRADEMARK OFFICE
CERTIFICATE OF CORRECTION

PATENT NO. : 9,884,129 B2
APPLICATION NO. : 14/589037
DATED : February 6, 2018
INVENTOR(S) : Jeffrey M. Karp, Debanjan Sarkar and Praveen Kumar Vemula It is certified that error appears in the above-identified patent and that said Letters Patent is hereby corrected as shown below:

On the Title Page

Item (71), delete "Women s" and insert -- Women's --

Signed and Sealed this
Seventeenth Day of April, 2018

Andrei Iancu
*Director of the United States Patent and Trademark Office*